United States Patent
Thumbikat et al.

(10) Patent No.: US 11,857,531 B2
(45) Date of Patent: Jan. 2, 2024

(54) COMBINATION MAST CELL INHIBITION FOR TREATMENT OF BPH/LUTS

(71) Applicant: Northwestern University, Evanston, IL (US)

(72) Inventors: Praveen Thumbikat, Chicago, IL (US); Anthony J. Schaeffer, Hinsdale, IL (US)

(73) Assignee: Northwestern University, Evanston, IL (US)

( * ) Notice: Subject to any disclaimer, the term of this patent is extended or adjusted under 35 U.S.C. 154(b) by 23 days.

(21) Appl. No.: 17/395,153

(22) Filed: Aug. 5, 2021

(65) Prior Publication Data
US 2022/0040143 A1    Feb. 10, 2022

Related U.S. Application Data

(60) Provisional application No. 63/173,050, filed on Apr. 9, 2021, provisional application No. 63/061,312, filed on Aug. 5, 2020.

(51) Int. Cl.
| | | |
|---|---|---|
| *A61K 31/352* | (2006.01) | |
| *A61P 13/08* | (2006.01) | |
| *A61K 31/495* | (2006.01) | |

(52) U.S. Cl.
CPC .......... *A61K 31/352* (2013.01); *A61K 31/495* (2013.01); *A61P 13/08* (2018.01)

(58) Field of Classification Search
CPC ...... A61K 31/352; A61K 31/495; A61P 13/08
See application file for complete search history.

(56) References Cited

U.S. PATENT DOCUMENTS

| | | | | |
|---|---|---|---|---|
| 2016/0058756 A1* | 3/2016 | Thumbikat | ............ | C07K 16/40 536/24.31 |
| 2019/0328700 A1 | 10/2019 | Gerhart et al. | | |

* cited by examiner

*Primary Examiner* — Timothy R Rozof
(74) *Attorney, Agent, or Firm* — Casimir Jones, S.C.; Rikki A. Hullinger

(57) ABSTRACT

Provided herein are compositions and methods for the treatment of conditions such as benign prostatic hyperplasia (BPH), Lower Urinary Tract Symptoms (LUTS), chronic prostatitis (CP) and/or chronic pelvic pain syndrome (CPPS). In particular, provided herein are combination therapies comprising a mast cell inhibitor and a histamine receptor antagonist.

3 Claims, 21 Drawing Sheets

Specification includes a Sequence Listing.

Normal        Hyperplasia

US 11,857,531 B2

COMBINATION MAST CELL INHIBITION FOR TREATMENT OF BPH/LUTS

STATEMENT REGARDING RELATED APPLICATIONS

This application claims priority to U.S. Provisional Patent Application No. 63/061,312, filed Aug. 5, 2020, and to U.S. Provisional Patent Application No. 63/173,050, filed Apr. 9, 2021, the entire contents of each of which are incorporated herein by reference.

STATEMENT REGARDING FEDERALLY SPONSORED RESEARCH

This invention was made with government support under grant number DK117906 awarded by the National Institutes of Health. The government has certain rights in the invention.

FIELD

Provided herein are compositions and methods for the treatment of conditions such as benign prostatic hyperplasia (BPH), Lower Urinary Tract Symptoms (LUTS), chronic prostatitis (CP) and/or chronic pelvic pain syndrome (CPPS). In particular, provided herein are combination therapies comprising a mast cell inhibitor and a histamine receptor antagonist.

BACKGROUND

BPH is a very common affliction, impacting the lives of millions of men through its causative role of LUTS and it is a huge socio-economic burden to the health care industry spending well over a billion dollars every year. Current medical treatments for this condition suffer from lack of effect or failure of therapeutic efficacy with time. Accordingly, what is needed are improved methods for treating BPH associated with LUTS (BPH/LUTS) in a subject.

SUMMARY

Provided herein are compositions and methods for the treatment of conditions such as benign prostatic hyperplasia (BPH), Lower Urinary Tract Symptoms (LUTS), chronic prostatitis (CP) and/or chronic pelvic pain syndrome (CPPS). In particular, provided herein are combination therapies comprising a mast cell stabilizer and a histamine receptor antagonist.

In some aspects, provided herein are compositions comprising a mast cell stabilizer and a histamine receptor antagonist. In some aspects, the compositions provided herein may be used in methods for the treatment or prevention of one or more conditions. In some embodiments, the compositions comprising a mast cell stabilizer and a histamine receptor antagonist may be used for the treatment or prevention of one or more conditions selected from benign prostatic hyperplasia, chronic prostatitis, and/or chronic pelvic pain syndrome. In some embodiments, the condition may be benign prostatic hyperplasia is associated with lower urinary tract symptoms. In some embodiments, the composition comprises a mast cell stabilizer and a histamine receptor antagonist. In some embodiments, the mast cell stabilizer is cromolyn sodium. In some embodiments, the histamine receptor antagonist is a histamine receptor 1 antagonist. For example, the histamine receptor 1 antagonist may be cetirizine. In some embodiments, the histamine receptor antagonist is a histamine receptor 2 antagonist. In particular embodiments, the composition for treatment or prevention of benign prostatic hyperplasia comprises cromolyn sodium and cetirizine.

In some aspects, provided herein are methods of treating or preventing benign prostatic hyperplasia in a subject. In some embodiments, the subject is afflicted with or at risk of developing benign prostatic hyperplasia associated with lower urinary tract symptoms. The methods comprise providing to the subject one or more inhibitors of mast cell function. In some embodiments, the one or more inhibitors of mast cell function are selected from a mast cell stabilizer, a histamine receptor 1 antagonist, and a histamine receptor 2 antagonist. In some embodiments, at least one of the inhibitors of mast cell function comprises a mast cell stabilizer. For example, the mast cell stabilizer may be cromolyn sodium. In some embodiments, at least one of the inhibitors of mast cell function is a histamine receptor 1 antagonist. For example, the histamine receptor 1 antagonist may be cetirizine. In some embodiments, at least one of the inhibitors of mast cell function is a histamine receptor 2 antagonist. In particular embodiments, the method of treating or preventing benign spastic hyperplasia in a subject comprises providing cromolyn sodium and cetirizine to the subject.

In some embodiments, provided herein are methods of treating or preventing chronic prostatitis (CP) and/or chronic pelvic pain syndrome (CPPS) in a subject, comprising providing to the subject an inhibitor of mast cell function and a histamine receptor 1 antagonist. In some embodiments, the subject is afflicted with or at risk of developing CP and/or CPPS. In some embodiments, the subject has tested positive for increased mast cell tryptase. In some embodiments, the inhibitor of mast cell function comprises a mast cell stabilizer. In some embodiments, the mast cell stabilizer is cromolyn sodium. In some embodiments, the histamine receptor 1 antagonist is cetirizine.

In some embodiments, provided herein are methods comprising testing a sample from a subject for mast cell tryptase and administering an inhibitor of mast cell function and a histamine 1 receptor antagonist to the subject to treat CP and/or CPPS. In some embodiments, the mast cell stabilizer is cromolyn sodium. In some embodiments, the histamine receptor 1 antagonist is cetirizine.

For any of the methods described herein, the subject may be human. In some embodiments, the subject is over the age of 50.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(FIG. 1A) Quantification of percentage of extracellular collagen deposition in hyperplasia—BPH and normal prostate tissues using NIH Image J software s, and (FIG. 1B) quantitated data for number of human mast cell tryptase positive mast cells in hyperplasia—BPH and normal prostate tissue. Each data point represents an individual patient tissue data, which is derived by averaging the counts and collagen contents for 3 different tissue biopsies for each patient (Mean±SEM; *, p<0.05; unpaired t-test). (FIG. 1C, FIG. 1D), representative images of prostate sections from normal control (left), and hyperplasia—BPH (right) patients under 10× magnification for picrosirius staining (FIG. 1C), and 4× magnification for human mast cell tryptase (FIG. 1D).

(FIG. 2A) a representative sample data graph from the Urovoid Analysis software showing the voiding measurements collected using the Urovoid system and how each of the parameters are calculated. The representative data shows the urine volume collected in weight (grams) over time (60 min.). The red arrows mark each individual void, the increase in weight per void is marked as void volume, and the time between each void is marked as Inter-micturition interval (IMI). (FIG. 2B) average number of voids per hour over a period of 4 hours; (FIG. 2C) average volume of urine per void (calculated for each animal individually); (FIG. 2D) average amount of time, in minutes, between each micturition event; and (FIG. 2E) average urine production rate (UPR) as defined as the volume of urine collected over the 4-hour period of time (indicating changes in the ability to produce urine) in control and CP1 infected C57BL/6 a day before and at days −5, −14, and −35 post-infection. (Mean±SEM; N=4 mice per group; #p<0.1, *p<0.05, **p<0.01; two-way ANOVA Fisher's LSD test)

(FIG. 3A) Total numbers of mast cells and (FIG. 3B) percentage of activated (fully and partial combined) mast cells in toluidine blue stained sections of mouse prostate lobes harvested at 5-, 14-, and 35-days' post CP1 infection (Mean±SEM; N=4 mice per group; p<0.01, *p<0.001, ****p<0.0001; two-way ANOVA Fisher's LSD test). The mast cell numbers and percentage of activated mast cells were determined by counting and averaging three sections of the mouse prostate stained with toluidine blue for each sample. (FIG. 3C) representative images of toluidine blue stained dorso-lateral prostate sections from control PBS instilled (left) and CP1 infected (right) mice at 35-day post instillation imaged at 10× and 40× magnification. Note the increased degranulation of mast cells (as denoted by less intracytoplasmic granular staining of mast cells) is marked by red arrow heads, while resting mast cells (with intact cytoplasm and membrane) is marked by red arrows.

(FIG. 4A) Schematic representation of treatment of mice with cromolyn sodium (CrS) and cetirizine di-hydrochloride (CeHCl). Mice given transurethral (t.u.) instillations of PBS or CP1 were treated intra-peritoneally (i.p.) with the combination of CrS+CeHCl daily for 10 days from day 4 or day 25 ("early treatment" and "late treatment" respectively) before assessment of the effects of combination treatment on various parameters. (FIG. 4B) Total numbers of mast cells and (FIG. 4C) percentage of activated (fully and partial combined) mast cells in toluidine blue stained sections of mouse prostate dorso-lateral lobes harvested at 14 (early) and 35 (late) days' post CP1 infection (Mean±SEM; each dot represents an individual mouse; p<0.01, *p<0.001, ****p<0.0001; one-way ANOVA Fisher's LSD test). The mast cell numbers and percentage of activated mast cells were determined by counting and averaging three sections of the mouse prostate lobes stained with toluidine blue for each sample.

(FIG. 5A) average number of voids per hour over a period of 4 hours; (FIG. B) average volume of urine per void (calculated for each animal individually); (FIG. 5C) IMI as measured by average amount of time, in minutes, between each micturition event; and (FIG. 5D) average urine production rate (UPR) in control, CP1 infected mice, and CrS+CeHCl treated CP1 infected mice at 14 ("early") and 35 ("late") days' post CP1 infection (Mean±SEM; each dot represents an individual mice; p<0.01, *p<0.001; one-way ANOVA Fisher's LSD test).

(FIG. 6E) mRNA expression levels for pro-fibrotic genes Col-1a1, 1a2, and 3a1 as well as TGFβ were examined from RNA isolated from total prostates of mice from control, CP1 infected mice, and CrS+CeHCl treated CP1 infected mice at 14 ("early") and 35 ("late") days' post CP1 infection. RNA was isolated, converted to cDNA, and subjected to real-time PCR analysis with the respective gene primers. The mRNA expression levels are normalized to GAPDH mRNA levels for each sample and the data are represented as fold change over control (Mean±SEM; each dot represents an individual mouse; *p<0.05, p<0.01, *p<0.001, ****p<0.0001; one-way ANOVA Fisher's LSD test).

(FIG. 7A) Flow cytometric gating strategy for analyzing the immune cell infiltrates in cell suspension prepared from whole prostates of mice. (FIG. 7B) Prostates isolated from control, CP1 infected mice, and CrS+CeHCl treated CP1 infected mice at 35 ("late") days' post CP1 infection were digested and total lymphocytes (CD45$^+$ cells), CD3$^+$ T-lymphocytes (as well as CD4$^+$ and CD8$^+$ T cells), CD11b$^+$ monocytes/macrophages, and CD11c$^+$ dendritic cells were stained with the respective fluorescent antibodies (as indicated in materials and methods) and analyzed by flow cytometry. Data represents total numbers of each cell type obtained from whole prostates using the tissue digestion protocol described in materials and methods (Mean±SEM; each dot represents an individual mouse; *p<0.05, p<0.01, *p<0.001; one-way ANOVA Fisher's LSD test).

(FIG. 9A) Whole-cell lysates were examined by Western blot analyses using the indicated antibodies, and a representative western blot for each group of mice at "early" times are shown. (FIG. 9B) quantifications of the Western blot data shown in FIG. 9A (n=8 "early" and n=7 "late"). The data plotted are arbitrary values obtained by normalizing the band intensity for the phosphorylated MLC2 to the band intensities of total MLC2 and then normalizing this to the band intensity of GAPDH, and the data are expressed as fold change over control (Mean±SEM; each dot represents an individual mouse; *$p<0.05$, $p<0.01$, *$p<0.001$; one-way ANOVA Fisher's LSD test).

DETAILED DESCRIPTION

Figures 1A, 1B:
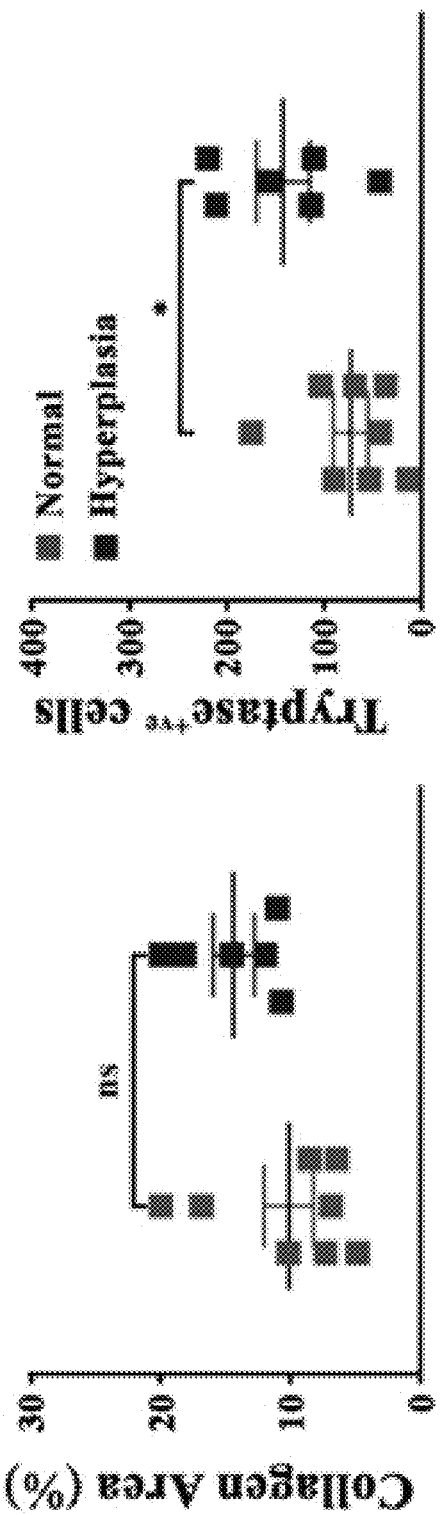
FIG. 1A-D. Increased fibrosis and mast cells numbers in prostates of BPH patients compared to normal control patients. Picrosirius staining for extracellular collagen deposition in human tissues (FIG. 1A & FIG. 1C) and IHC for human mast cell tryptase was used to assess numbers of mast cells (FIG. 1B & FIG. 1D) (from US Biomax, Inc.; catalog #PR632).
Figure 1C:
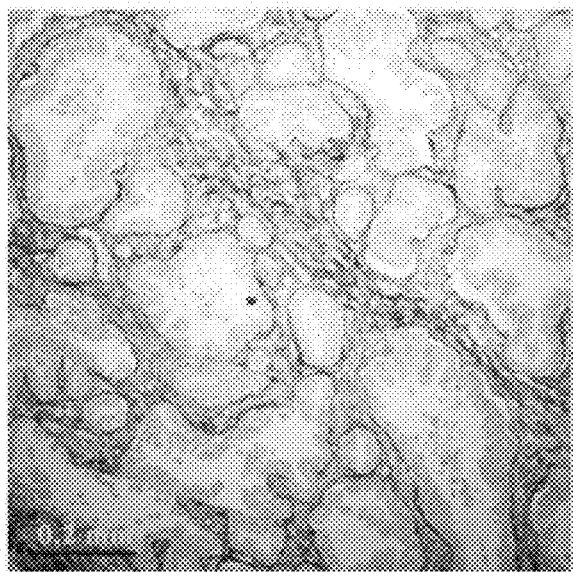
Figure 1C:
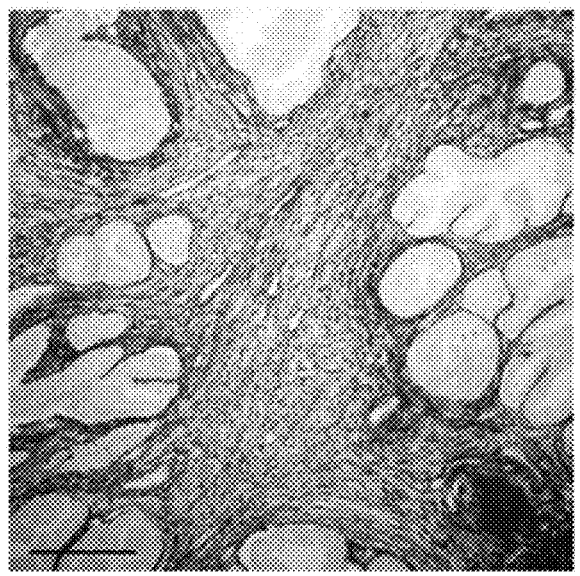
Figure 1D:
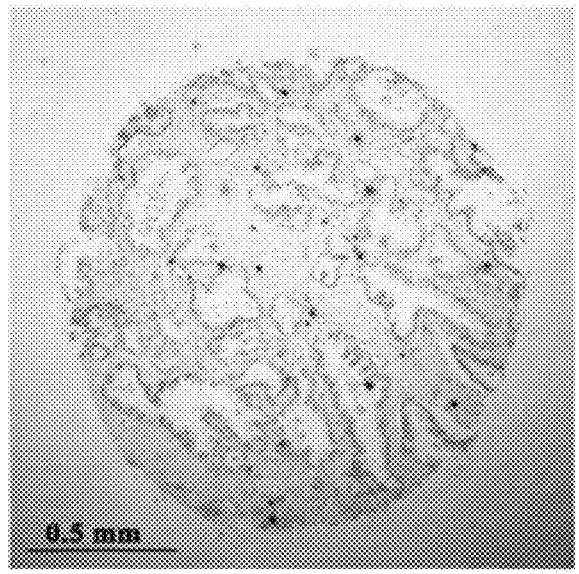
Figure 1D:
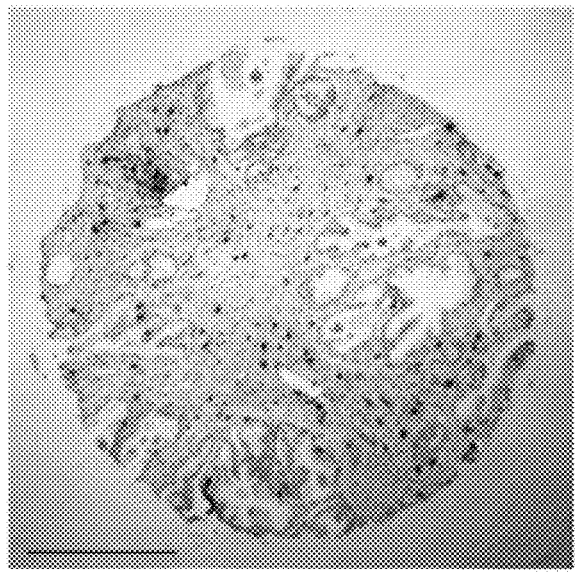

Provided herein are compositions and methods for the treatment of conditions such as benign prostatic hyperplasia (BPH), Lower Urinary Tract Symptoms (LUTS), chronic prostatitis (CP) and/or chronic pelvic pain syndrome (CPPS). In particular, provided herein are combination therapies comprising a mast cell stabilizer and a histamine receptor antagonist.

1. Definitions

Although any methods and materials similar or equivalent to those described herein can be used in the practice or testing of embodiments described herein, some preferred methods, compositions, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a peptide amphiphile" is a reference to one or more peptide amphiphiles and equivalents thereof known to those skilled in the art, and so forth.

As used herein, the terms "comprise", "include", and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, a "control" or a "control subject" refers to a subject that is not afflicted with benign prostatic hyperplasia, chronic prostatitis, and/or chronic pelvic pain syndrome. Accordingly, a "control" sample may be obtained from a control subject and used as a baseline from which levels of mast cell tryptase may be compared to evaluate whether or not a subject would benefit from treatment with an inhibitor of mast cell function as described herein.

As used herein, the term "benign prostatic hyperplasia" or "BPH" refers to a noncancerous increase in size of the prostate gland. Symptoms may include frequent urination, trouble starting to urinate, weak stream, inability to urinate, or loss of bladder control. Complications can include urinary tract infections, bladder stones, and chronic kidney problems. BPH is the most common cause of lower urinary tract symptoms (LUTS) in men.

As used herein, the term "lower urinary tract symptoms" or "LUTS" refers to any symptom associated with urine storage, voiding, or symptoms that occur after urination. Exemplary storage symptoms include frequent urination, waking at night to urinate, urgency (i.e. a compelling need to void that cannot be deferred), involuntary urination, or urge incontinence (i.e. urine leak following a strong sudden need to urinate). Voiding symptoms include urinary hesitancy (i.e. a delay between trying to urinate and urine flow beginning), intermittency (i.e. non-continuous urination), involuntary interruption of voiding, weak urinary stream, straining to void, a sensation of incomplete emptying, and uncontrollable leaking after the end of urination. These symptoms may be accompanied by bladder pain or pain while urinating, called dysuria.

The term "chronic prostatitis" as used herein refers to inflammation of the prostate. In some embodiments, chronic prostatitis refers to inflammation of the prostate that continues for at least 3 months. In humans, chronic prostatitis is often painful and can affect sexual function and/or the ability to urinate.

The term "chronic pelvic pain" as used herein refers to pelvic, perineal, and/or genital pain. In some embodiments, chronic pelvic pain refers to pain that lasts for 3 months or longer. In some embodiments, chronic pelvic pain refers to pain that lasts for 6 months or longer. The pain may be constant. The pain may be intermittent (e.g. relapsing and remitting). Chronic pelvic pain may be associated with urinary or sexual dysfunction.

The term "mast cell" as used herein refers to a type of granulocyte derived from the myeloid stem cell that is a part of the immune and neuroimmune systems. Mast cells are characterized by containing many granules rich in histamine and heparin.

The term "mast cell degranulation" refers to the cellular process by which chemicals are released from mast cell granules. For example, mast cell degranulation refers to the process by which inflammatory molecules, such as histamine and various cytokines, are released from granules. In some embodiments, a "mast cell stabilizer" inhibits mast cell degranulation, thereby preventing the release of histamine and other inflammatory molecules. A "mast cell stabilizer" may therefore be referred to herein as an "inhibitor of mast cell degranulation."

As used herein, the term "subject" refers to any animal (e.g., a mammal), including, but not limited to, humans, non-human primates, rodents, and the like, Which is to be the recipient of a particular treatment. Typically, the terms "subject" and "patient" are used interchangeably herein in reference to a human subject. In some embodiments, the subject may be over the age of 50.

As used herein, the terms "treat," "treatment," and "treating" refer to reducing the amount or severity of a particular condition, disease state (e.g., BPH), or symptoms thereof, in a subject presently experiencing or afflicted with the condition or disease state. The terms do not necessarily indicate complete treatment (e.g., total elimination of the condition, disease, or symptoms thereof). "Treatment," encompasses any administration or application of a therapeutic or technique for a disease (e.g., in a mammal, including a human), and includes inhibiting the disease, arresting its development, relieving the disease, causing regression, or restoring or repairing a lost, missing, or defective function; or stimulating an inefficient process.

As used herein, the terms "prevent," "prevention," and preventing" refer to reducing the likelihood of a particular condition or disease state from occurring in a subject not presently experiencing or afflicted with the condition or disease state (e.g., BPH). The terms do not necessarily indicate complete or absolute prevention. For example, "prevention" refers to reducing the likelihood of a condition or disease state occurring in a subject not presently experiencing or diagnosed with the condition or disease state. In order to "prevent" a condition or disease state, a composition or method need only reduce the likelihood of the condition or disease state, not completely block any possibility thereof "Prevention," encompasses any administration or application of a therapeutic or technique to reduce the likelihood of a disease developing (e.g., in a mammal, including a human). Such a likelihood may be assessed for a population or for an individual.

As used herein, the terms "co-administration" and "co-administering" refer to the administration of at least two agent(s) or therapies to a subject (e.g., a mast cell stabilizer and a histamine receptor antagonist). In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

2. Compositions and Methods for Treating Conditions

In some aspects, provided herein are compositions. In some embodiments, the composition comprises one or more inhibitors of mast cell function. In some embodiments, the composition comprises a mast cell stabilizer and a histamine receptor antagonist. In some embodiments, the compositions are used in a method of treating and/or preventing one or more conditions. In some embodiments, the conditions are selected from benign prostatic hyperplasia, chronic prostatitis, and chronic pelvic pain syndrome in a subject.

In some aspects, provided herein are methods of treating and/or preventing one or more conditions in a subject, comprising providing to a subject one or more inhibitors of mast cell function. In some embodiments, the conditions are selected from benign prostatic hyperplasia, chronic prostatitis, and chronic pelvic pain syndrome in a subject.

For any of the embodiments described herein, the subject may be afflicted with or at risk of developing benign prostatic hyperplasia, chronic prostatitis, and/or chronic pelvic pain syndrome. In some embodiments, the condition is benign spastic hyperplasia (BPH). In some embodiments, the BPH is associated with LUTS. BPH associated with LUTS may be referred to herein as "BPH/LUTS". In some embodiments, the subject is a male. In some embodiments, the subject is over the age of 50. In some embodiments, the subject has increased levels of mast cell tryptase compared to a control subject. In some embodiments, provided herein is a method comprising testing a sample obtained from a subject for mast cell tryptase, and administering a mast cell stabilizer and a histamine 1 receptor antagonist to the subject to treat chronic prostatitis (CP) and/or chronic pelvic pain syndrome (CPPS) when the levels of mast cell tryptase are increased compared to a control.

For any of the embodiments described herein, the inhibitor of mast cell function may be a mast cell stabilizer. In some embodiments, an inhibitor of mast cell function inhibits mast cell degranulation. Suitable mast cell stabilizers for use in the disclosed compositions and methods include, for example, cromolyn, dihydropyridines such as nicardipine and nifedipine, lodoxamide, nedocromil, bamidipine, YC-114, elgodipine, niguldipine, ketotifen, methylxanthines, quercetin, and pharmaceutically salts thereof. In some embodiments, the mast cell stabilizer is a pharmaceutically acceptable salt of cromolyn, such as cromolyn sodium, cromolyn lysinate, ammonium cromolyn, and magnesium cromoglycate. In some embodiments, the mast cell stabilizer is cromolyn sodium.

Cromolyn (5,5'-(2-hydroxypropane-1,3-diyl)bis(oxy)bis(4-oxo-4H-chromene-2-carboxylic acid)) is also referred to as cromoglicic acid. Cromolyn has the formula $C_{23}H_{16}O_{11}$. Cromolyn is commonly marketed as cromolyn sodium ($C_{23}H_{14}Na_2O_{11}$), the structure of which is shown below:

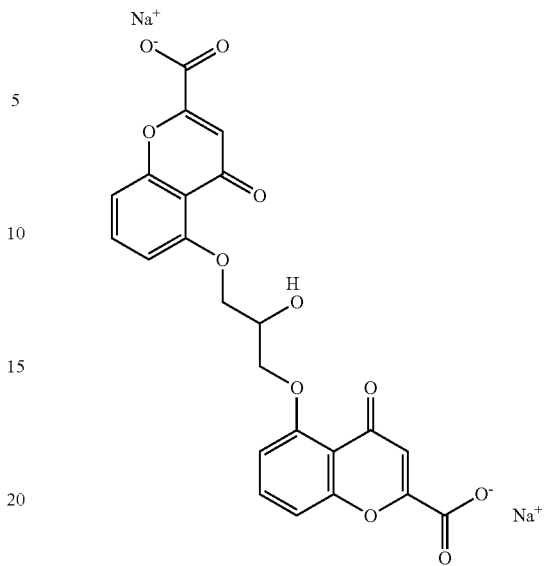

The mast cell stabilizer (e.g. cromolyn or a salt thereof) may be formulated in a suitable manner for administration to a subject by any suitable route. For example, the mast cell stabilizer (e.g. cromolyn sodium) may be formulated as a liquid composition. As another example, the mast cell stabilizer may be formulated as a solid composition. The mast cell stabilizer may be delivered by any suitable route, including but not limited to oral, rectal, nasal, topical (including transdermal, buccal and sublingual), vaginal, parenteral (including subcutaneous, intramuscular, intravenous and intradermal) and pulmonary administration. In some embodiments, the mast cell stabilizer may be administered intranasally (e.g. via inhalation). In some embodiments, the mast cell stabilizer may be formulated into a solid or a liquid formulation for oral administration. In some embodiments, the mast cell stabilizer is formulated for parenteral administration.

In some embodiments, the inhibitor of mast cell function inhibits the release of histamine from mast cells. In some embodiments, an inhibitor of mast cell function is an inhibitor of a histamine receptor. In some embodiments, an inhibitor of mast cell function is a histamine receptor 1 antagonist. Suitable histamine receptor 1 antagonists for use in the disclosed compositions include, for example, azelastine, clemastine, diphenhydramine, doxylamine, loratadine, desloratadine, fexofenadine, pheniramine, cetirizine, ebastine, promethazine, chlorpheniramine, levocetirizine, quetiapine, meclizine, terfenadine, dimenhydrinate, and salts and derivatives thereof in some embodiments, the histamine receptor 1 antagonist is cetirizine or a salt or derivative thereof.

In some embodiments, the histamine receptor 1 antagonist is cetirizine (2-[2-[4-[(4-chlorophenyl)-phenylmethyl]piperazin-1-yl]ethoxy]acetic acid) or a salt or derivative thereof, such as cetirizine hydrochloride. Cetirizine has the formula $C_{21}H_{25}ClN_2O_3$ is a metabolite of hydroxyzine and is a selective histamine receptor 1 antagonist. The structure of cetirizine is shown below:

In some embodiments, the histamine receptor antagonist is loratadine or a derivative thereof, such as desloratadine. Loratadine has the formula $C_{22}H_{23}ClN_2O_2$. The structure of loratadine is shown below:

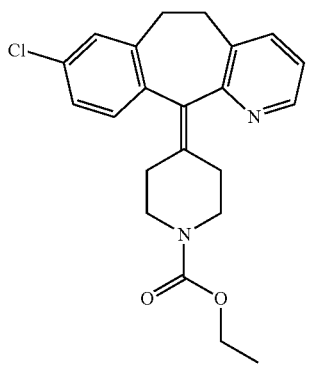 [SMILES: CCOC(=O)N1CCC(=C2c3ccc(Cl)cc3CCc3cccnc32)CC1]

In some embodiments, the histamine 1 receptor antagonist is desloratadine. Desloratadine ($C_{19}H_{19}ClN_2$) is a metabolic derivative of loratadine, and has the structure:

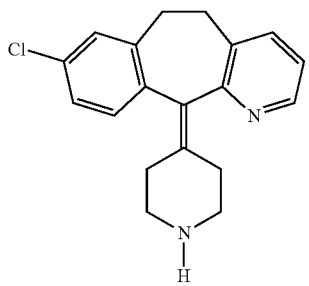 [SMILES: Clc1ccc2c(c1)CCc1cccnc1C2=C1CCNCC1]

In some embodiments, the histamine 1 receptor antagonist fexofenadine ($C_{32}H_{39}NO_4$). Fexofenadine is a long-lasting histamine 1 receptor antagonist, and has the structure:

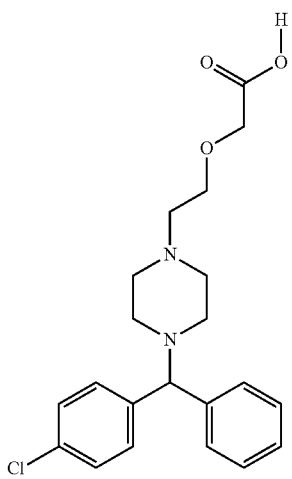

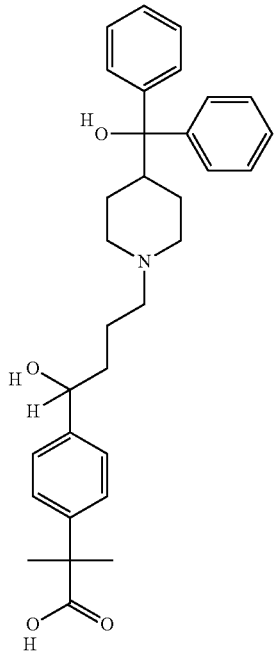

In some embodiments, an inhibitor of mast cell function is a histamine receptor 2 antagonist. In some embodiments, suitable histamine receptor 2 antagonists for use in the disclosed compositions include, cimetidine, famotidine, ranitidine, nizatidine, roxatidine, lafutidine, and derivatives thereof. In some embodiments, a histamine receptor 2 antagonist is ranitidine. Ranitidine has the formula $C_{13}H_{22}N_4O_3S$, and the structure is shown below:

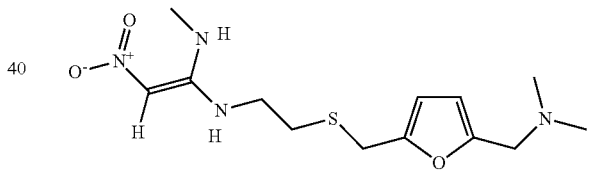

The histamine receptor 1 or histamine receptor 2 antagonist may be formulated as a suitable composition for delivery to a subject by any suitable route. For example, the antagonist may be formulated as a liquid composition. As another example, the antagonist may be formulated as a solid composition. As with the mast cell stabilizer, the histamine receptor 1 or histamine receptor 2 antagonist may be administered to the subject by any suitable route, including but not limited to oral, rectal, nasal, topical (including transdermal, buccal and sublingual), vaginal, parenteral (including subcutaneous, intramuscular, intravenous and intradermal) and pulmonary administration. In some embodiments, the antagonist may be administered intranasally (e.g. via inhalation). In some embodiments, the antagonist may be formulated into a solid or a liquid formulation for oral administration. In some embodiments, the antagonist may be administered parenterally.

In some embodiments, the compositions comprise a mast cell stabilizer (e.g. cromolyn sodium) and a histamine receptor 1 antagonist (e.g. cetirizine). In some embodiments, the compositions comprise a mast cell stabilizer (e.g. cromolyn sodium) and a histamine receptor 2 antagonist. In some embodiments, the methods for treating the one or more conditions comprise providing to the subject a mast cell stabilizer and a histamine receptor 1 antagonist. For example, in some embodiments, the methods for treating BPH, CP, and/or CPPS comprise providing to the subject cromolyn sodium and cetirizine.

Any suitable amount of the one or more inhibitors of mast cell function may be provided to the subject to achieve the intended result. Compositions comprising the one or more inhibitors of mast cell function may comprise one or more suitable excipients. Suitable excipients may be selected based upon the intended delivery route to the subject. The compositions described herein may conveniently be presented in unit dosage form, may be prepared according to conventional techniques well known in the pharmaceutical industry. Such techniques include the step of bringing into association the active ingredients with the pharmaceutical carrier(s) or excipient(s). In general, compositions are prepared by uniformly and intimately bringing into association the active ingredients (e.g. inhibitors of mast cell function) with liquid carriers or finely divided solid carriers or both, and then, if necessary, shaping the product.

In some embodiments, the one or more inhibitors of mast cell function are provided to the subject in the same composition (e.g. provided concurrently in a single composition). For example, in some embodiments the mast cell stabilizer and the histamine receptor 1 antagonist are provided to the subject in the same composition. In some embodiments, the one or more inhibitors of mast cell function are provided to the subject in separate compositions. For example, in some embodiments the mast cell stabilizer and the histamine receptor 1 antagonist are provided to the subject in separate compositions. When separate compositions are administered, the route of administration for each composition may be the same. Alternatively, the route of administration for each composition may differ.

In some embodiments, the inhibitors of mast cell function are formulated together into a single composition (e.g. pill, topically-administered liquid, inhalant, liquid for parenteral administration, etc.). In some embodiments, the inhibitors of mast cell function formulated together within a composition are configured for separate therapeutic release regimens (e.g. timed release, delayed release, immediate release, etc.). In some embodiments, the inhibitors of mast cell function formulated together within a composition are configured for immediate effectiveness. In some embodiments, the inhibitors of mast cell function are formulated as separate compositions to be co-administered. In some embodiments, co-administration comprises administering separate compositions simultaneously, or near simultaneously. In some embodiments, co-administration comprises a therapeutic strategy in which a subject is administered separate compositions, but not necessarily concurrently.

The one or more inhibitors of mast cell function may be provided to the subject at any suitable dose. Dosing may be dependent on the age of the subject, the weight of the subject, the route of administration, the severity and responsiveness of the disease state to be treated, etc. The course of treatment may last from several days to several months, or until a cure is affected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models or based on the examples described herein.

In general, dosage is from 0.01 µg to 100 g per kg of body weight, and may be given once or more in a suitable dosing regimen. For example, the dosage may be given to the subject multiple times in a day (e.g. two or more times per day, three or more times per day, four or more times per day, five or more times per day, etc.), once daily, every other day, every three days, every four days, every five days, every six days, weekly, every two weeks, every three weeks, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the composition is administered in maintenance doses, ranging from 0.01 µg to 100 g per kg of body weight, at a suitable dosage schedule for a suitable duration of time to achieve the desired effect.

In some embodiments, the dose of the mast cell stabilizer is about 10 µg/kg to about 20 mg/kg. For example, the dose of cromolyn sodium may be about 10 µg/kg, about 20 µg/kg, about 30 µg/kg, about 40 µg/kg, about 50 µg/kg, about 60 µg/kg, about 70 µg/kg, about 80 µg/kg, about 90 µg/kg, about 100 µg/kg, about 150 µg/kg, about 200 µg/kg, about 250 µg/kg, about 300 µg/kg, about 350 µg/kg, about 400 µg/kg, about 450 mg/kg, about 500 µg/kg, about 550 µg/kg, about 600 µg/kg, about 650 µg/kg, about 700 µg/kg about 750 µg/kg, about 800 µg/kg, about 850 µg/kg, about 900 µg/kg, about 950 µg/kg, about 1 mg/kg about 2 mg/kg, about 3 mg/kg about 4 mg/kg, about 5 mg/kg about 6 mg/kg, about 7 mg/kg, about 8 mg/kg, about 9 mg/g, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, or about 20 mg/kg.

In some embodiments, the dose of the histamine 1 or histamine 2 receptor antagonist is about 10 µg/kg to about 300 µg/kg. For example, in some embodiments the dose of the histamine 1 or histamine 2 receptor antagonist is about 10 µg/kg, about 20 µg/kg, about 30 µg/kg, about 40 µg/kg, about 50 µg/kg, about 60 µg/kg, about 70 µg/kg, about 80 µg/kg, about 90 µg/kg, about 100 µg/kg, about 110 µg/kg, about 120 µg/kg, about 130 µg/kg, about 140 µg/kg, about 150 µg/kg, about 200 µg/kg, about 250 µg/kg, or about 300 µg/kg.

In some embodiments, compositions and methods of the present invention are provided prophylactically (e.g. to prevent development of BPH, CP, CPPS, and/or symptoms thereof). In some embodiments, compositions and methods of the present invention are provided therapeutically (e.g. to treat BPH, CP, and/or CPPS or symptoms thereof in a subject suffering from BPH, CP, and/or CPPS). In some embodiments, compositions and methods of the present invention provide palliative treatment (e.g. reduction in the symptoms of BPH, CP, and/or CPPS). In some embodiments, compositions and methods of the present invention provide curative treatment (e.g. elimination of BPH, CP, and/or CPPS in a subject). In some embodiments, compositions and methods of the present invention provide preventative treatment (e.g. prevent the development of BPH, CP, and/or CPPS in a subject).

The compositions and methods described herein may be provided to a subject or performed on a subject in combination with other suitable therapies for the treatment and/or prevention of BPH, chronic prostatitis, and/or chronic pelvic pain syndrome. Other suitable therapies include, for example, behavioral modifications including physical activity, decreasing fluid intake before bedtime, moderating the consumption of alcohol and caffeine-containing products, and following a timed voiding schedule. Other suitable therapies may also include additional therapeutic agents, including $\alpha_1$-blockers (e.g. alfuzosin, doxazosin, silodosin, amsulosin, tetrazosin, naftopidil), 5α-reductase inhibitors (e.g. finasteride, dutasteride), phosphodiesterase-5 inhibitors (e.g., tadalafil, sildenafil), antimuscarinics (e.g. tolterodine), and the like.

EXPERIMENTAL

Example 1

Materials and Methods
Mice

Figure 2A:
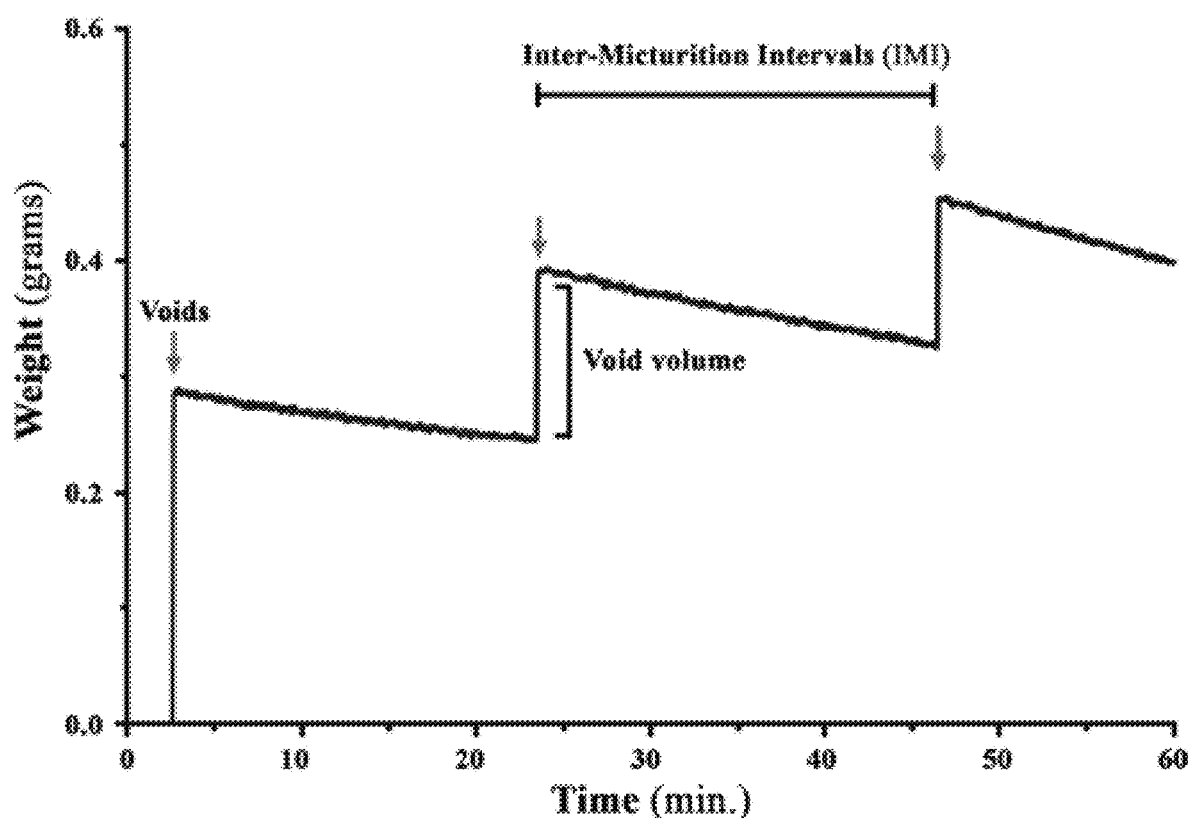
FIG. 2A-E. An *E. coli* (CP1)-induced mouse model of LUTS recapitulates and induces urinary dysfunction in mice.
Figure 4A:
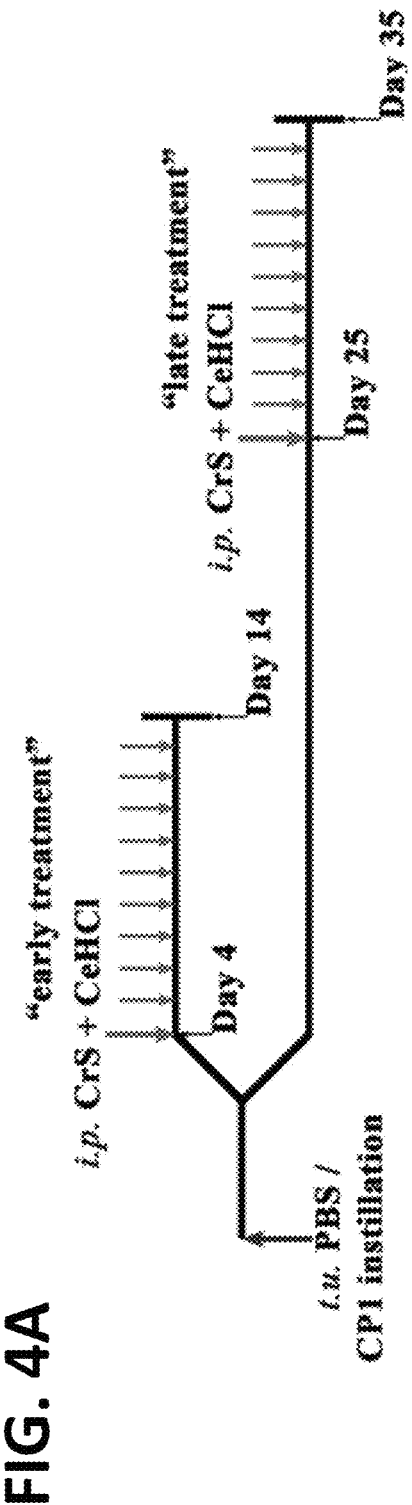
FIG. 4A-C. Combination treatment of cromolyn sodium and cetirizine di-hydrochloride inhibits mast cell activation in the prostates of CP1 infected mice.

Male C57BL/6 mice (5-7 weeks of age) were obtained from Jackson Laboratory. Mice were housed in a single environmentally controlled room within the Northwestern University animal facility. All animal experiments and procedures have been approved by the Northwestern University Animal Care and Use Committee.
Trans-Urethral Mice Infections Mouse infections were performed as described previously (28-30). Briefly, CP1 *E. coli* bacteria were grown in LB overnight shaking at 37° C., followed by overnight static subculture at 37° C. The next day, bacteria were concentrated at $2\times10^{10}$ bacterial/mL in PBS, and 10 μL ($2\times10^8$ bacteria) was instilled transurethrally into isoflurane-anesthetized male C57BL/6 mice. Age-matched control male C57BL/6 animals received a transurethral (t.u.) instillation of PBS (Gibco, Paisley, UK) and were kept in separate cages.
Voiding Behavior Testing To assess the voiding behavior of mice, the Urovoid system (Med Associates, Fairfax, VT, USA) was utilized, a noninvasive means of measuring voiding function using a modified procedure previously described (31). The Urovoid system is designed to assess conscious urinary voiding behavior (frequency and voiding volume) in unrestrained mice for prolonged periods without the need for surgery or catheter implantation. Briefly, mice were singly housed in chambers access to water for 5 hours. Urine was collected below the grated cage on a balance [mice feces is separated using a mesh above the balance], and urine weight was recorded over time (1-hour post housing the mice to allow for acclimatization). After the completion of these measurements, animals were returned to their home cages for future experimentation or euthanized as per experimental design. The data collected was then using the Urovoid voiding frequency analysis system (Med Associates, Fairfax, VT, USA). A representative graph from the analysis software is shown in FIG. 2A.
Mouse Tissue Preparation The prostates were harvested from mice after euthanizing as described previously (32). Depending on the experimental design, each prostate sample (separated by lobes) were either fixed in 10% formalin or frozen at −80° C. in TRIzol™ reagent (Life Technologies Corporation, Grand Island, NY, USA), or frozen at −80° C. in 1×RIPA (Santa Cruz Biotechnology, Dallas, TX, USA) containing complete-EDTA protease inhibitor cocktail and phosSTOP phosphatase inhibitor (Millipore-Sigma, Burlington, MA, USA), or processed for tissue digestion for flow cytometry. Formalin samples were further processed and embedded in paraffin. The formalin-fixed paraffin-embedded (FFPE) samples were then sectioned (5 μm sections) and mounted on glass slides for staining.
In Vivo Administration of Mast Cell Stabilizer and Histamine 1 Receptor Antagonist Male C57BL/6 mice were intra-peritoneally treated starting at either 5- or 25-days' post-infection ["prophylaxis" or "treatment" groups respectively] with either cetirizine dihydrochloride at 2.5 mg/kg (histamine 1 receptor antagonist), or cromolyn sodium salt at 0.5 mg/kg (mast cell stabilizer) (Sigma, St. Louis, MO, USA), or a combination of both at the same concentrations daily for 10 days as illustrated in (FIG. 4A). Following voiding behavior testing on days 14 or 35 ["early treatment" or "late treatment" groups respectively], mice were euthanized and tissues were prepared as described above.
Histological and Immunohistochemical Assays All histological and IHC staining and assays were performed on the anterior, ventral, and dorsolateral separately. 5 μm sections were processed for H&E staining. Briefly, H&E staining on FFPE tissues were performed on a fully automated platform (Leica Autostainer XL; Lecia Biosystems, Buffalo Grove, IL, USA) using Harris Hematoxylin (Fisher Scientific, Hampton, NH, USA) and Eosin secondary counter stain (Lecia Biosystems, Buffalo Grove, IL, USA). Prostate inflammation was assessed using the classification system as described previously (34). Inflammation scoring was quantitated as follows: 0—no inflammation, 1—mild inflammation, 2—moderate inflammation, and 3—severe inflammation. Inflammation was scored by three independent scorers in a masked manner, averaged and presented in the graphs. For assessing extracellular collagen deposition, picrosirius staining was performed as previously described (28). Briefly, 5 μm prostate sections on glass slides were rehydrated, and slides were stained in picrosirius red solution (Direct Red 80 and saturated picric acid, Sigma, St. Louis, MO, USA) for 16 hours. The sections were washed in two changes of acidified water, dehydrated in ethanol, cleared in xylene, and mounted with Krystalon (EMD Millipore, MA, USA). Stained sections were quantitated using NIH Image J software and percentage of collagen deposition were calculated. Toluidine blue staining was used, a metachromatic stain should stain mast cells red-purple (metachromatic staining) and the background blue (orthochromatic staining) for the identification of mast cells. Briefly, 5 μm prostate sections on glass slides were rehydrated, and sections were stained using 0.1% toluidine blue for 2-3 minutes, washed thrice using distilled water, dehydrated in ethanol, cleared in xylene, and mounted with Krystalon (EMD Millipore, MA, USA). Stained cells were counted in a masked manner to quantitate levels of resting and activated mast cells. IHC staining of mouse mast cells in the prostate tissues were carried using rat anti-mouse MCP-8 Antibody (catalog #647401, RRID: AB_2069309, BioLegend®, San Diego, CA, USA), a protease primarily expressed in mouse basophils (35). Briefly, FFPE tissue slides were deparaffinized on an automated platform (Leica Autostainer XL; Lecia Biosystems, Buffalo Grove, IL, USA). Slides are treated with an antigen retrieval step using a sodium citrate solution at pH 6, in a pressure cooker. Sections were incubated overnight at 4° C. with human mast cell tryptase antibody in a humid chamber. All IHC staining was completed using chromogenic enzyme substrate reactions with DAB (Agilent Technologies, Santa Clara, CA, USA). Secondary antibody incubation and chromogenic reactions are then performed using an automated INTELLIPATH FLX system (Biocare Medical, Pacheco, CA, USA). Once the staining was completed, specimens were counterstained with Hematoxylin (Fisher Scientific, Hampton, NH, USA) and mounted using a xylene based mounting medium (Lecia Biosystems, Buffalo Grove, IL, USA).

Bright-field images and circularly polarized images were taken on a Leica DMLA microscope (Leica Microsystems Inc., Buffalo Grove, IL, USA) using a QImaging MicroPublisher 3.3 RTV camera (Teledyne Photometrics, Tucson, AZ, USA) and analyzed on Micro-manager, an open-source microscopy software (36).

Human Tissue Microarray

The tissue arrays of Human prostate normal as well as hyperplasia punch biopsy sections (PR632) were purchased from US Biomax Inc. (Derwood, MD, USA). The patient data as provided by US Biomax Inc., are as follows. The prostate tissues for the normal control samples were obtained from healthy donors post autopsy between the ages of 28 to 48. The prostate tissue biopsies for the 6 cases of BPH were obtained from patients who were in their older adulthood (ages 58 to 78) with dysuria for several months or years or clinical symptoms of prostate hypertrophy and pathology diagnosis showed that these samples had benign hyperplasia. Picrosirius staining for the sections were performed as described above. IHC staining of mast cell tryptase was carried using mouse anti-human Mast Cell Tryptase Antibody (catalog #369402, RRID:AB_2566541, BioLegend®, San Diego, CA, USA). IHC staining was performed as described above.

Flow Cytometry

Figure 7A:
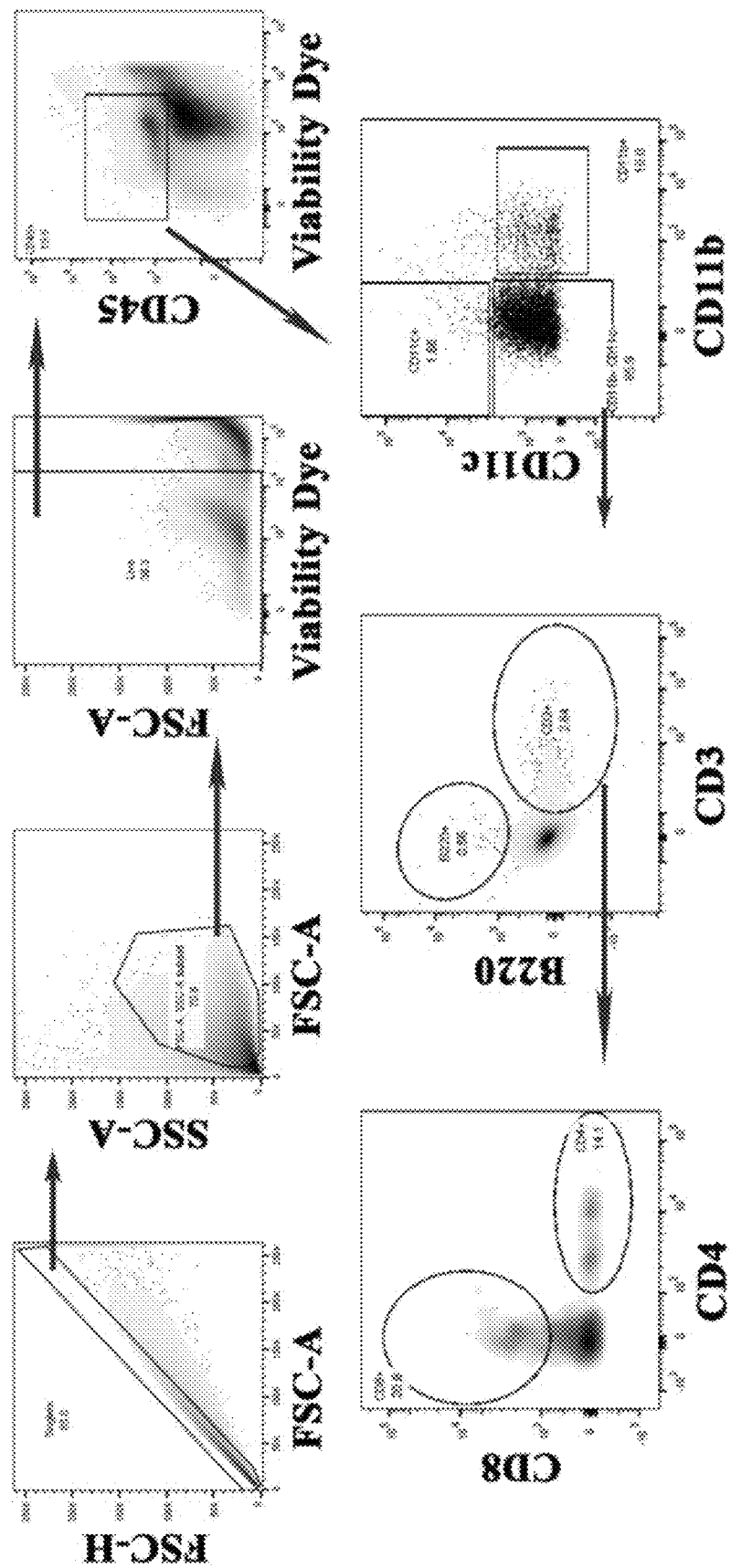
FIG. 7A-B. Mast cell inhibition mollifies alterations in CP1-induced immune cell infiltrates in the prostate of mice.

Single-cell suspensions were generated from whole prostate tissues combining all prostate lobes using a modified procedure previously described (37). Briefly, whole prostates (combining all lobes) were dissected under sterile conditions from euthanized mice and collected in 1×HBSS buffer containing 5 mM EDTA (Life Technologies Corporation, Grand Island, NY, USA) and 2% FBS (Hyclone, South Logan, UT, USA). Prostates were incubated in a shaker for 15 min. at 37° C. to loosen the tissue. Then the tissues were spun down at 100×g and minced with fine scissors. The tissues were then dissociated by shaking for 45 min. at 37° C. in a 0.4 µm filtered solution of 0.5 mg/mL collagenase D (Roche, Indianapolis, IN, USA), 1 Unit/mL Dispase (Stemcell Technologies, Vancouver, BC, Canada), and 0.1 mg/mL DNase I (Sigma, St. Louis, MO, USA) in 1×HBSS. Digestions were subsequently filtered through a 40 µm nylon mesh and washed with 1×PBS twice before counting and proceeding to stain the cells. After washing, cells were incubated with Zombie UV™ fixable viability kit (BioLegend®, San Diego, CA, USA). Following which, cells were washed in FACS buffer (2% FCS in PBS) and staining performed using the following conjugated antibodies: Brilliant Violet™ (BV)510CD11c (catalog #117353, RRID:AB_2686978), BV570-CD8 (catalog #100740, RRID:AB_2563055), BV650-CD3 (catalog #100229, RRID:AB_11204249), AlexaFluor700-CD45 (catalog #103128, RRID:AB_493715), PerCP-B220 (catalog #103234, RRID:AB_893353), PE/Dazzle™594-CD4 (catalog #100566, RRID:AB_2563685) (BioLegend®, San Diego, CA), and APC/Cy7-CD11b (catalog #557657, RRID: AB_396772; BD Biosciences, San Jose, CA, USA). Samples were run on a BD LSRFortessa™ (BD Biosciences, San Jose, CA, USA) cytometer and analyzed using FlowJo™. The gating strategy for all the samples is shown in FIG. 7A.

Real-Time Quantitative Reverse-Transcriptase PCR

Total RNA was isolated using TRIzol™ reagent (Life Technologies Corporation, Grand Island, NY, USA), and cDNA synthesis, starting with 1 µg of total RNA, was performed with random hexamers using High-Capacity cDNA Reverse Transcription Kit (Life Technologies Corporation, Grand Island, NY, USA) per the manufacturer's instructions. Primers for quantitative PCR (qPCR) were created for the RNA of interest using the NIH online primer blast tool. Reverse Transcription-Quantitative Polymerase Chain Reaction (RT-qPCR) reactions were performed using SsoAdvanced™ universal SYBR® green (Bio-Rad, Hercules, CA, USA) and run on the CFX Connect (Bio-Rad, Hercules, CA, USA) platform. A full table of primer sequences is included in Table 1. The data were analyzed by the $2^{-\Delta\Delta C_T}$ method (38), and normalized to GAPDH as the housekeeping gene. The data are represented as fold change normalized to the average expression of the gene of interest in their respective control group.

TABLE 1

List of primer pairs used for quantitative real-time PCR.

| Gene Target | | Primer sequence |
|---|---|---|
| GAPDH | F | GCTGACCTGCTGGATTACATT (SEQ ID NO: 1) |
|  | R | GTTGAGAGATCATCTCCACCA (SEQ ID NO: 2) |
| IL-4 | F | CCATATCCACGGATGCGACA (SEQ ID NO: 3) |
|  | R | CGTTGCTGTGAGGACGTTTG (SEQ ID NO: 4) |
| IL-13 | F | GTATGGAGTGTGGACCTGGC (SEQ ID NO: 5) |
|  | R | TCTGGGTCCTGTAGATGGCA (SEQ ID NO: 6) |
| STAT-6 | F | ACGACAACAGCCTCAGTGTGGA (SEQ ID NO: 7) |
|  | R | CAGGACACCATCAAACCACTGC (SEQ ID NO: 8) |
| IFNγ | F | ACGGCACAGTCATTGAAAGC (SEQ ID NO: 9) |
|  | R | ACCATCCTTTTGCCAGTTCC (SEQ ID NO: 10) |
| IL-17a | F | CAGACTACCTCAACCGTTCCAC (SEQ ID NO: 11) |
|  | R | TCCAGCTTTCCCTCCGCATTGA (SEQ ID NO: 12) |
| IL-10 | F | ATTTGAATTCCCTGGGTGAGAAG (SEQ ID NO: 13) |
|  | R | CACAGGGGAGAAATCGATGACA (SEQ ID NO: 14) |
| Col 1a1 | F | CGATGGATTCCCGTTCGAGT (SEQ ID NO: 15) |
|  | R | GAGGCCTCGGTGGACATTAG (SEQ ID NO: 16) |
| Col 1a2 | F | AGTCGATGGCTGCTCCAAAA (SEQ ID NO: 17) |
|  | R | GCAATGTCAAGGAACGGCAG (SEQ ID NO: 18) |
| Col 3a1 | F | AAGGGCGAAGATGGCAAAGA (SEQ ID NO: 19) |
|  | R | AGCCACTAGGACCCCTTTCT (SEQ ID NO: 20) |

TABLE 1-continued

List of primer pairs used for
quantitative real-time PCR.

| Gene Target | | Primer sequence |
|---|---|---|
| TGFβ | F | GGACTCTCCACCTGCAAGAC (SEQ ID NO: 21) |
| | R | CTGGCGAGCCTTAGTTTGGA (SEQ ID NO: 22) |

Western Blotting

Frozen prostate samples were lysed in 1×RIPA lysis buffer (Santa Cruz Biotechnology, Dallas, TX, USA) containing complete-EDTA protease inhibitor cocktail and phosSTOP phosphatase inhibitor (Millipore-Sigma, Burlington, MA, USA). Cell lysates were cleared by centrifugation at 14,000 rpm for 30 min at 4° C., and insoluble debris was discarded. Proteins were separated by SDS-PAGE on Criterion 4-20% mini gels (Bio-Rad, Hercules, CA, USA), transferred to polyvinylidene fluoride membranes (Bio-Rad, Hercules, CA, USA), blocked, and probed with the respective Abs. Immunoblotting was performed using the following antibodies—mouse anti-phospho myosin light chain 2 (Ser19) (catalog #3675, RRID:AB_2250969), rabbit anti-human myosin light chain 2 (D18E2) [with cross-reactivity to mouse] (catalog #8505, RRID:AB_2728760; Cell Signaling Technology, Danvers, MA, USA), and goat anti-human GAPDH [with cross-reactivity to mouse] (catalog #AF5718, RRID:AB_2278695; R&D Systems, Inc., Minneapolis, MN, USA); and developed using SuperSignal™ west -pico or -femto chemiluminescence kit (Thermo Fisher, Hampton, NH, USA). The protein bands were quantified using the National Institutes of Health ImageJ software package and expressed as values of phosphorylated proteins normalized to total species and then to GAPDH levels.

Statistical Analyses

Statistical analyses were performed using GraphPad Prism™ (GraphPad Software, San Diego, CA, USA). Statistical tests utilized in each experiment, technical replicates, biological replicates, independent repeat experiments performed, and murine n values are indicated in figure legends (in most figures, each dot represents individual animals). Data are represented as the mean±standard deviation (SD) or mean±standard error of the mean (S.E.M.) as appropriate. #$p<0.1$, *$p<0.05$, $p<0.01$, *$p<0.001$, ****$p<0.0001$.

Results

Elevated Mast Cell Numbers are Observed in Human BPH Tissues

Fibrosis, as observed by collagen deposition captured by picrosirius staining, was examined in prostate tissue biopsy sections from human BPH patients and controls obtained from US Biomax, Inc. (Cat #PR632). Patients with BPH show an increase in immune cell infiltration as compared to controls (as shown in the company product specification images). Extracellular collagen deposition, a marker for fibrosis in tissue (41), showed an increase but non-significant trend (p value <0.1) in the prostate tissue of BPH patients compared to normal controls (FIG. 1, A&C; C—representative picrosirius images comparing surgical BPH and control normal prostate tissue). Mast cell numbers were quantified by immunostaining for mast cell tryptase in prostate tissue biopsy sections from BPH patients and controls. These results show a significant increase in mast cells in prostate tissues from patients with BPH compared to controls (FIG. 1, B&D; D—representative IHC images comparing surgical BPH and control normal prostate tissue). This observation implies that mast cells may affect BPH development and progression.

Urinary Dysfunction in the CP1-Induced Mouse Model of LUTS is Associated with Activation of Mast Cells and an Increase in Mast Cell Numbers in the Prostate Here, in addition to showing that instillation of CP1 induces voiding dysfunction, it was determined whether there were associated changes in mast cell numbers and activation status in the prostates of mice.

Figure 2B:
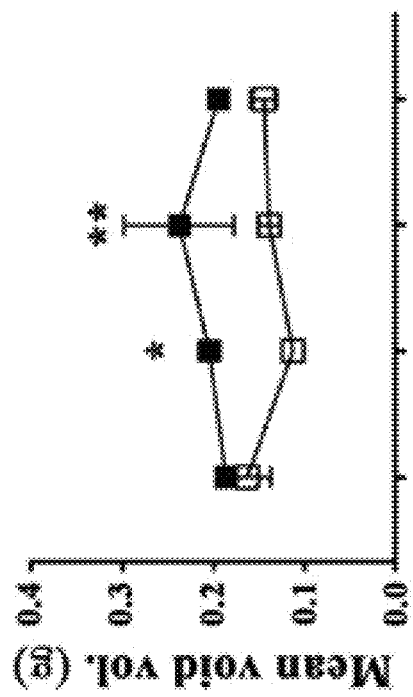
Figure 2C:
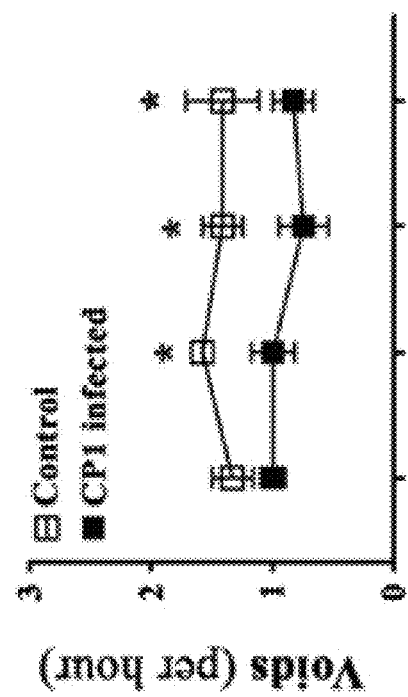
Figure 2D:
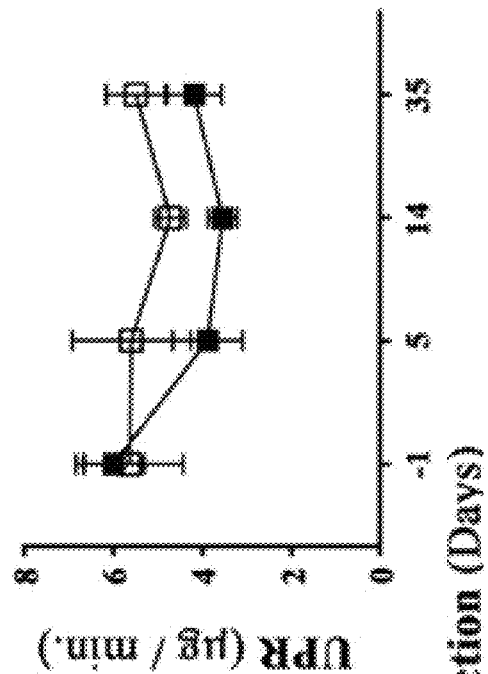
Figure 2E:
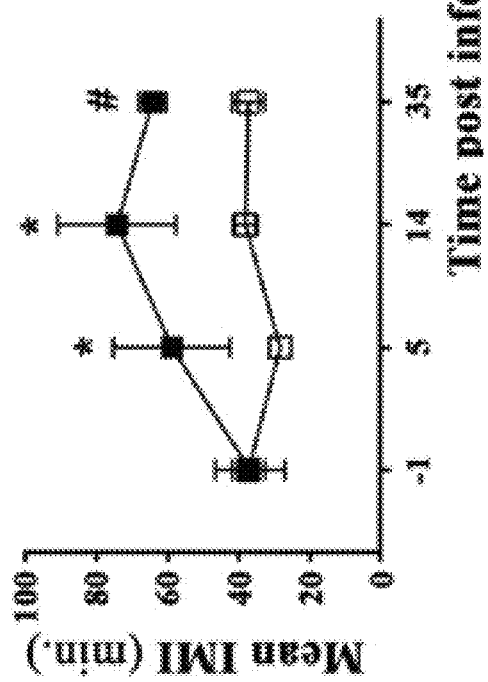

To determine effects on voiding behavior, the urovoid system was used, a noninvasive approach to assess conscious urinary voiding behavior of mice (31). Representative data from the Urovoid analysis software that was utilized to determine the inter-micturition interval (IMI) and void mass (volume) per void in CP1-infected C57BL/6 animals over time (FIG. 2A). Following instillation with CP1, a significant reduction in the average number of urinary voids at days 5, 14, and 35 was observed compared to control non-infected mice. (FIG. 2B). Conversely, the average urinary void mass and IMI were significantly increased in mice at days 5, and 14 (and not at day 35) following instillation with CP1 compared to control mice (FIG. 2, C-D). The urine production rate (UPR) for both groups of mice remain the same over time, indicating that the mice do not have an infection induced intrinsic deficit in the production of urine (FIG. 2E).

Figures 3A, 3B:
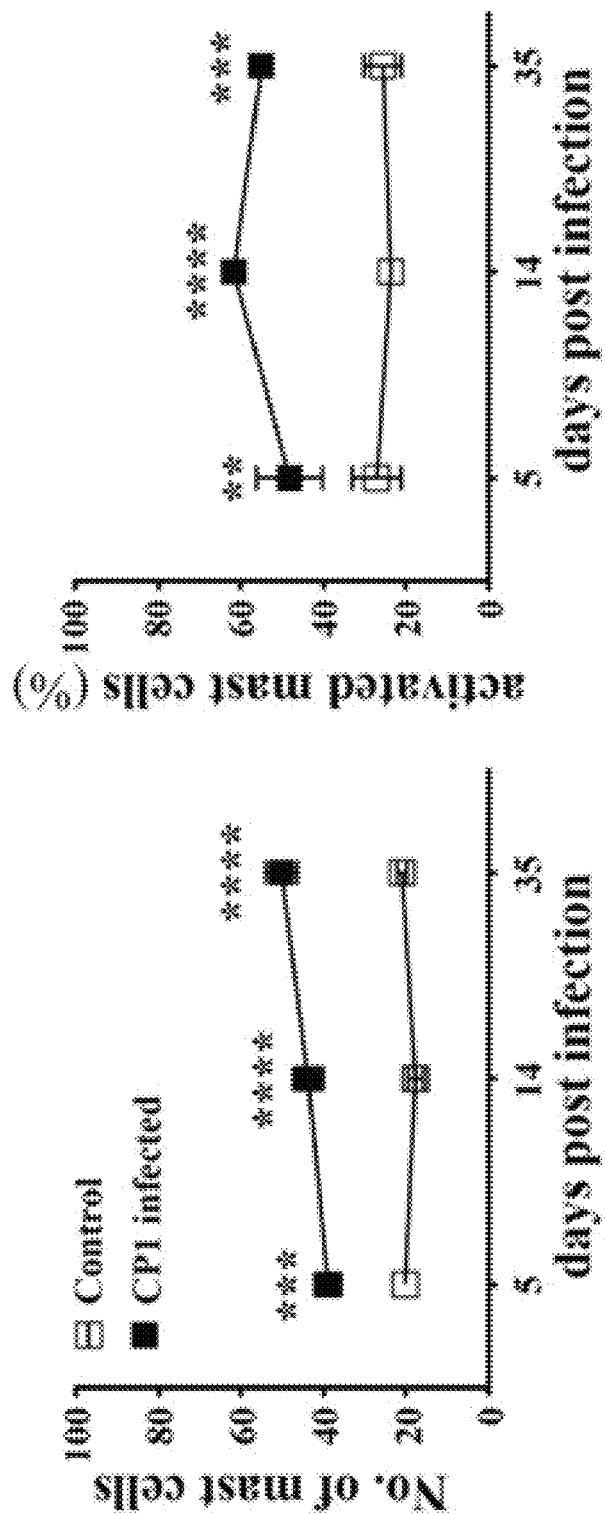
FIG. 3A-C. CP1 infection triggers an increase mast cell numbers and its activation in the prostate of mice.
Figure 3C:
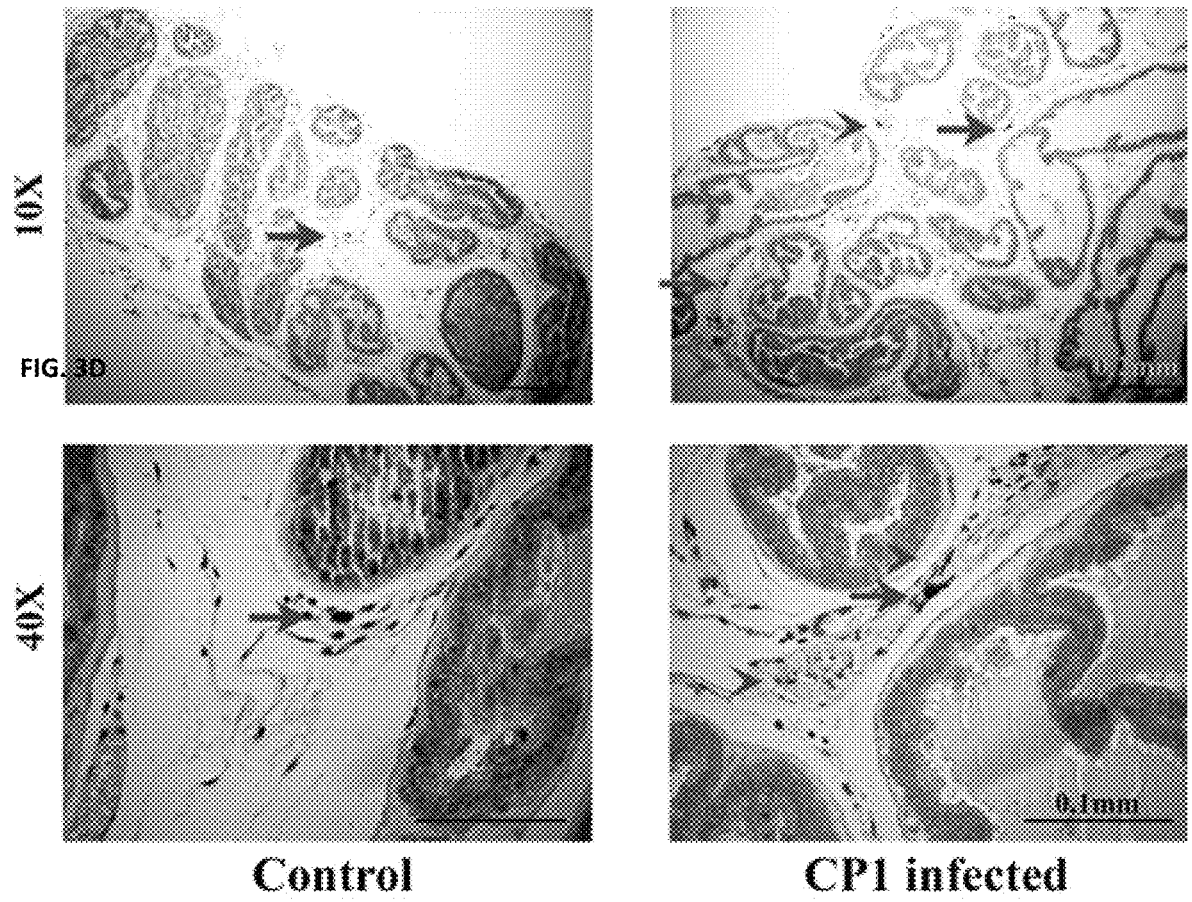

To assess the role of mast cells, the prostates of CP1-infected mice were examined to determine the numbers and activation status of mast cells. Prostate sections from CP1 infected mice and control mice were subjected to toluidine blue staining to assess mast cell numbers and activation status in the lobes of the prostate. A significant increase in the mast cell numbers in the prostate sections at days 5, 14, and 35 was observed compared to control mice, and in particular, the increase in mast cell numbers was most striking in the dorsolateral lobe of the prostate (FIG. 3A). Furthermore, an accumulation of mast cells in the prostates over the 35-day time period post CP1 instillation was observed. The activation status of these mast cells was assessed by quantitating the number of degranulated mast cells as compared to resting mast cells and determining the percentage of activated mast cells in the prostate sections. Following CP1 instillation, a significant increase in the percentage of activated mast cells in the prostate sections as days 5, 14, and 35 compared to control mice was shown (FIG. 3B), suggesting that CP1 infection causes increased degranulation of mast cells. FIG. 3C shows representative toluidine blue staining images of dorsolateral prostate tissues from control and CP1 infected C57BL/6 at day 35 post-infection showing increased mast cell infiltrates as well increased activated mast cells in the prostate tissues of CP1 infected mice. It is noticeable that the increased infiltration of mast cells as well as activation of mast cells following CP1 instillation is most pronounced in the dorsolateral lobe of the prostate which is supportive of the evidence showing increased inflammation score in the dorsolateral lobe upon CP1 infection.

Since toluidine blue is a stain that binds strongly to the granules in both mast cells and basophils, it was assessed whether basophils are present in the prostates of mice in this *E. coli* induced model of prostate fibrosis. The prostate tissues were stained for basophils using mouse mast cell protease 8 (mMCP-8); which despite its name is expressed highly in basophils, but is expressed at negligible levels by mast cells, neutrophils, and basophils (35, 43). Following CP1 instillation, at 35 days' post-instillation, no observable infiltration of basophils in the dorso-lateral lobe of the prostate was seen (FIG. 11). This suggests that basophils play a negligible role in this model of prostate inflammation and fibrosis.

Mast Cell Stabilizer and Histamine 1 Receptor Inhibition Prevents Mast Cell Activation and Alleviates Urinary Dysfunction in CP1 Infected Mice To test whether preventing mast cell activation and mast cell downstream signaling histamine signaling might be an effective strategy at reducing or reversing markers of pathology, mice were administered a combination of a mast cell stabilizer (MCS), cromolyn sodium salt (CrS), and a histamine receptor 1 antagonist (H1RA), cetirizine di-hydrochloride (CeHCl) intra-peritoneally for 10 days daily starting at either 5- or 25-days (early and late respectively) post-infection (FIG. 4A).

Figure 4C:
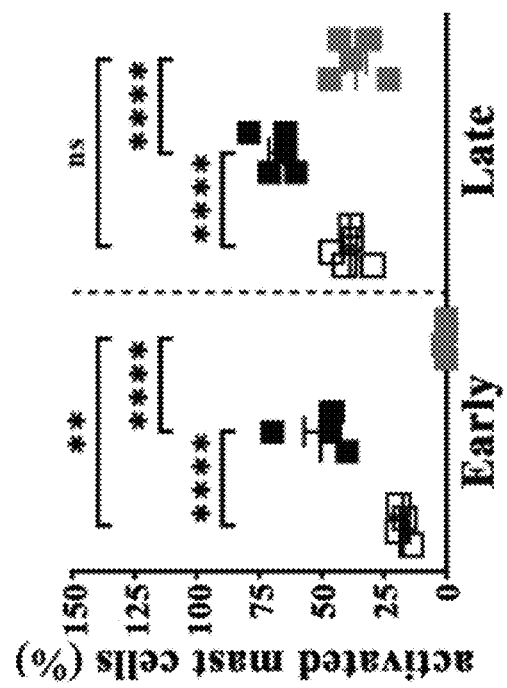
Figure 4B:
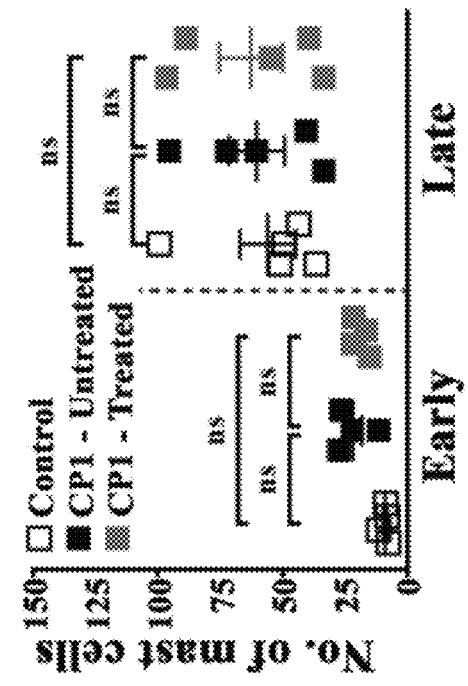

To determine whether this combination therapy is effective in preventing mast cell activation, the numbers and activation status of mast cells in prostate lobes from CrS+CeHCl treated CP-infected mice was compared to CP1-infected mice using toluidine blue staining of prostate sections. In both the "early treatment" and the "late treatment" groups, while there are little changes in the mast cell numbers in the combined prostate lobes of CrS+CeHCl treated CP1 infected mice as compared to CP1 infected mice, a significant decrease in the % of activated mast cells following both "early" and "late" treatment (FIG. 4, B-C) was seen.

Figure 5A:
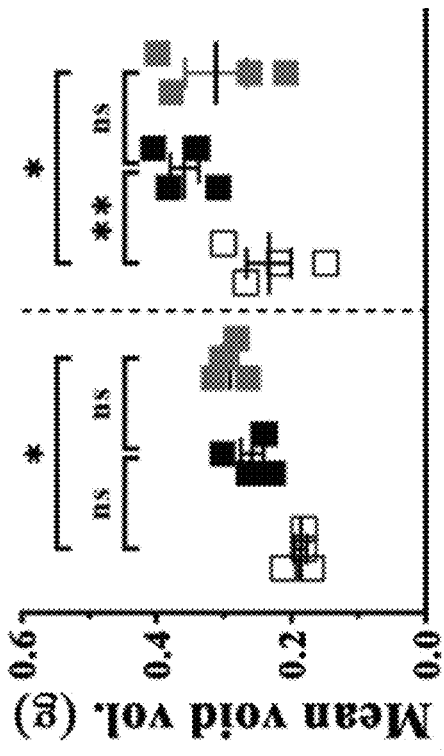
FIG. 5A-D. Mast cell inhibition alleviates urinary dysfunction in CP1 infected mice.
Figure 5B:
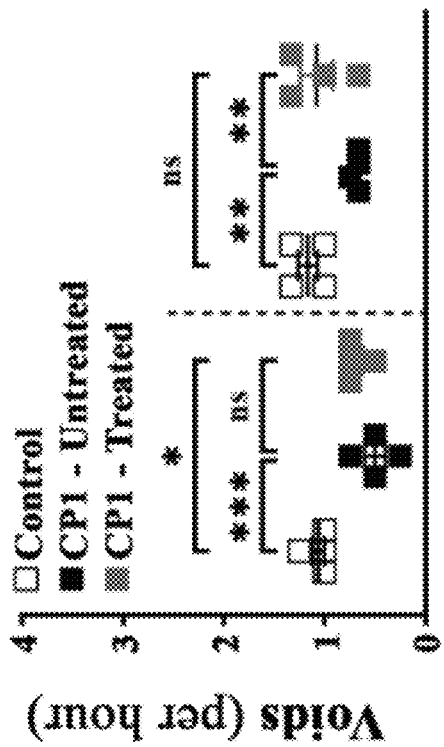
Figure 5C:
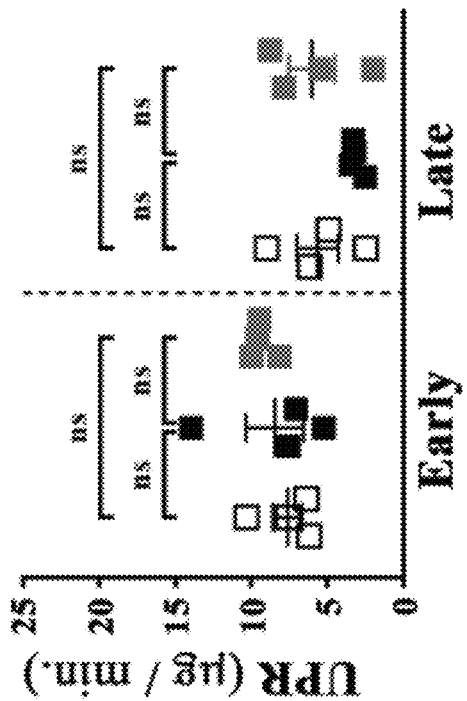
Figure 5D:
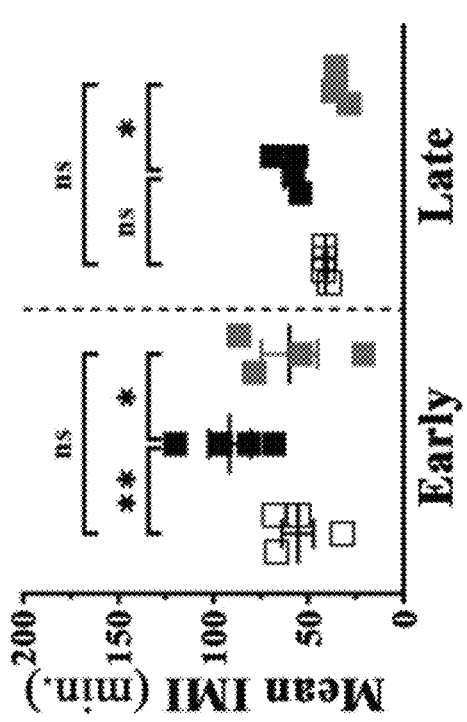

The voiding behavior in CP1-infected mice post mast cell and histamine 1 receptor inhibition was next evaluated using the urovoid system. Similar to earlier observations (FIG. 2), following CP1 instillation mice experienced urinary dysfunction as observed by decreased average number of urinary voids in both "early" and "late" treatment groups (FIG. 5A), along with increased mean void mass and IMI (FIG. 5, B-C). Following 10-day i.p. administration of the combination of CrS+CeHCl, the average number of urinary voids in CP1-infected mice were significantly increased comparable to that of control mice in the "late" treatment group (FIG. 5A). Furthermore, in both the "early" and "late" treatment groups, a significant decrease in IMI that was similar to control mice (FIG. 5C) was seen. Interestingly, the average urinary void mass of CP1-infected mice treated with CrS+CeHCl did not show any difference as compared to untreated CP1-infected mice in both "early" and "late" treatment groups (FIG. 5B). The UPR for all the groups of mice remains the same at "early" and "late" time points (FIG. 5.D). These data suggest treatment for inhibition of mast cell degranulation along with histamine 1 receptor inhibition (here in referred to as mast cell inhibition) leads to significant alleviation in CP1-induced urinary dysfunction in mice.

Mast Cell Inhibition Ameliorates Fibrosis in Prostates of CP1 Infected Mice

Figures 6A, 6B:
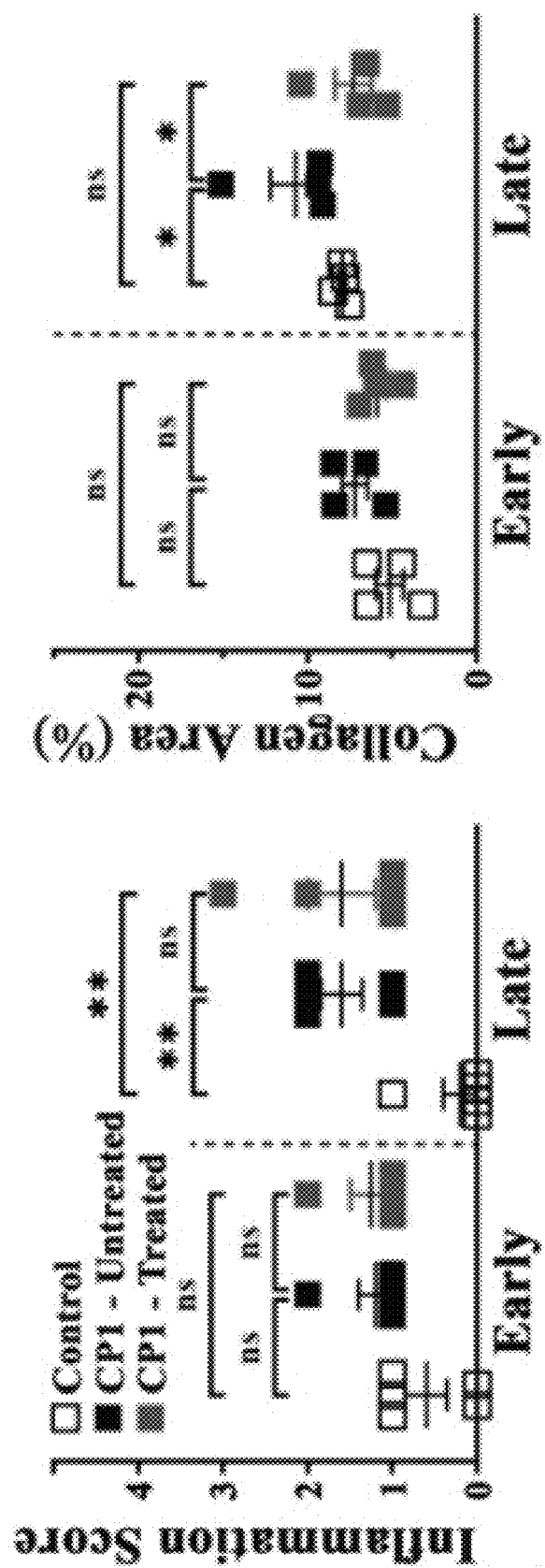
FIG. 6A-E. Inflammation and fibrosis is driven by mast cell activity in CP1-induced mouse model of LUTS. Quantitation of (FIG. 6A) inflammation score (as described in the materials and methods) using H&E staining, and (FIG. 6B) percentage of extracellular collagen deposition as assessed by picrosirius staining from sections of the dorso-lateral lobe of the prostates from control, CP1 infected mice, and CrS+CeHCl treated CP1 infected mice at 14 ("early") and 35 ("late") days' post CP1 infection (Mean±SEM; each dot represents an individual mouse; *p<0.05, **p<0.01; one-way ANOVA Fisher's LSD test). The inflammation score and percentage of collagen area were obtained by examining three independent sections of the mouse prostate lobes stained with H&E and picrosirius red staining respectively. Quantification of picrosirius staining was performed using NIH Image J software. Representative H&E images (FIG. 6C) and picrosirius images (FIG. 6D) of dorso-lateral prostate sections from control PBS instilled (top), CP1 infected (middle), and mast cell inhibitor treated CP1 infected (bottom) mice at 35-days post instillation imaged 4× magnification. The increased infiltration and immune cell foci is marked by black arrow heads (FIG. 6C).
Figure 6C:
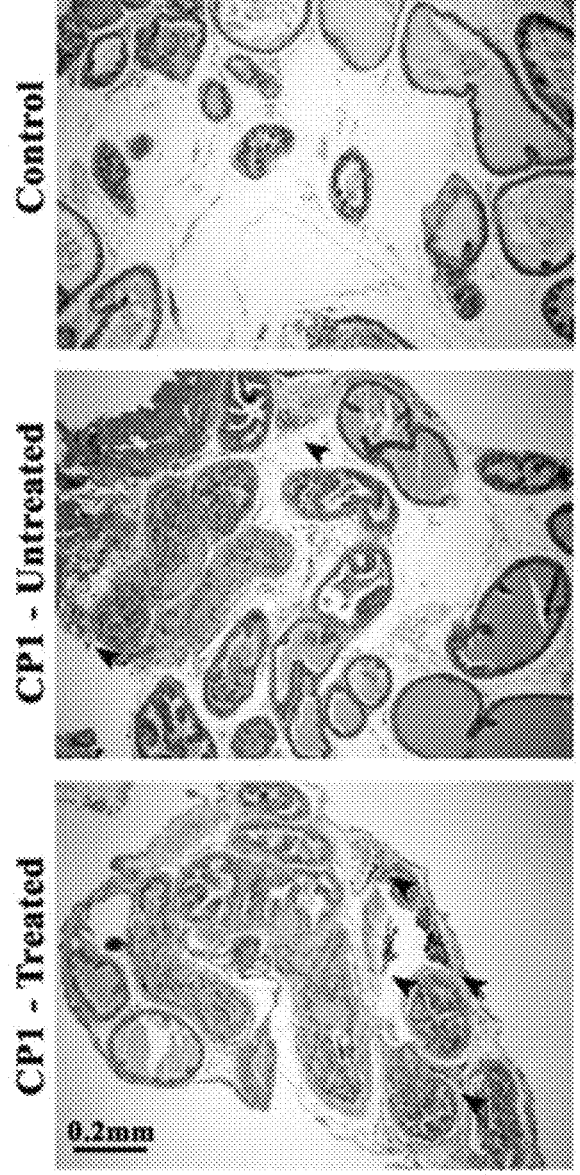

To understand the mechanism by which mast cell inhibition alleviates urinary dysfunction, inflammation and fibrosis was assessed in MCS+H1RA treated CP1-infected mice. Inflammation in prostate tissue from CrS+CeHCl treated CP1-infected mice, CP1 infected mice, and control mice was evaluated by staining sections from the prostate lobes using H&E. CP1 instillation in C57BL/6 mice triggers a modest but significant level of inflammation in the prostate sections from the dorso-lateral lobe of mice at day 35 ("late" group) compared to control mice (FIG. 6A). Upon mast cell inhibition, no significant changes in the inflammation scores in both the "early" and "late" treatment group (FIG. 6A) were observed. FIG. 6C shows representative H&E images of sections from the dorsolateral lobe of prostate tissues from control, CP1-infected, and CP1-infected CrS+CeHCl treated C57BL/6 at day 35 post-infection showing infiltration of immune cells in the stroma of the prostates.

Figure 6D:
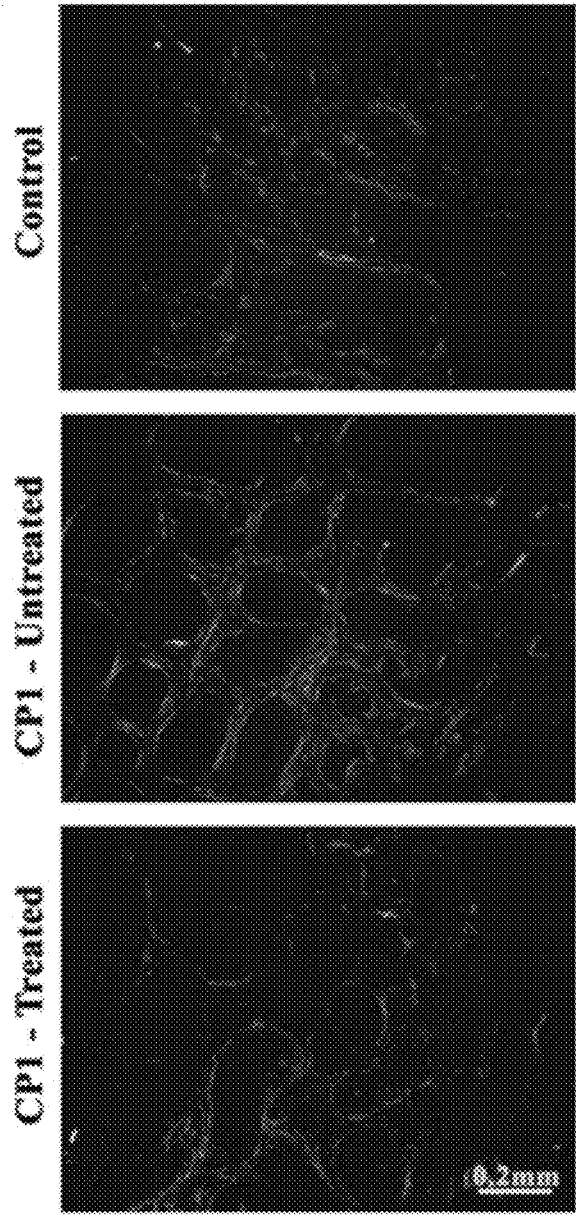

Next, the extent of extracellular collagen deposition in each lobe of the infected mouse prostates was examined. Extracellular collagen deposition in the dorsolateral lobes of prostates of CP1 infected mice at day 35 post infection is shown in FIG. 6B. Therapeutic administration of CrS+CeHCl in CP1 infected mice (significantly at "late treatment" and to a lesser extent "early treatment") is able to attenuate CP1 induced collagen deposition (FIG. 6B). FIG. 6D shows representative picrosirius images of sections from the dorsolateral lobe of prostate tissues from control, CP1-infected, and CP1-infected CrS+CeHCl treated C57BL/6 at day 35 post-infection showing collagen deposition.

Figure 6E:
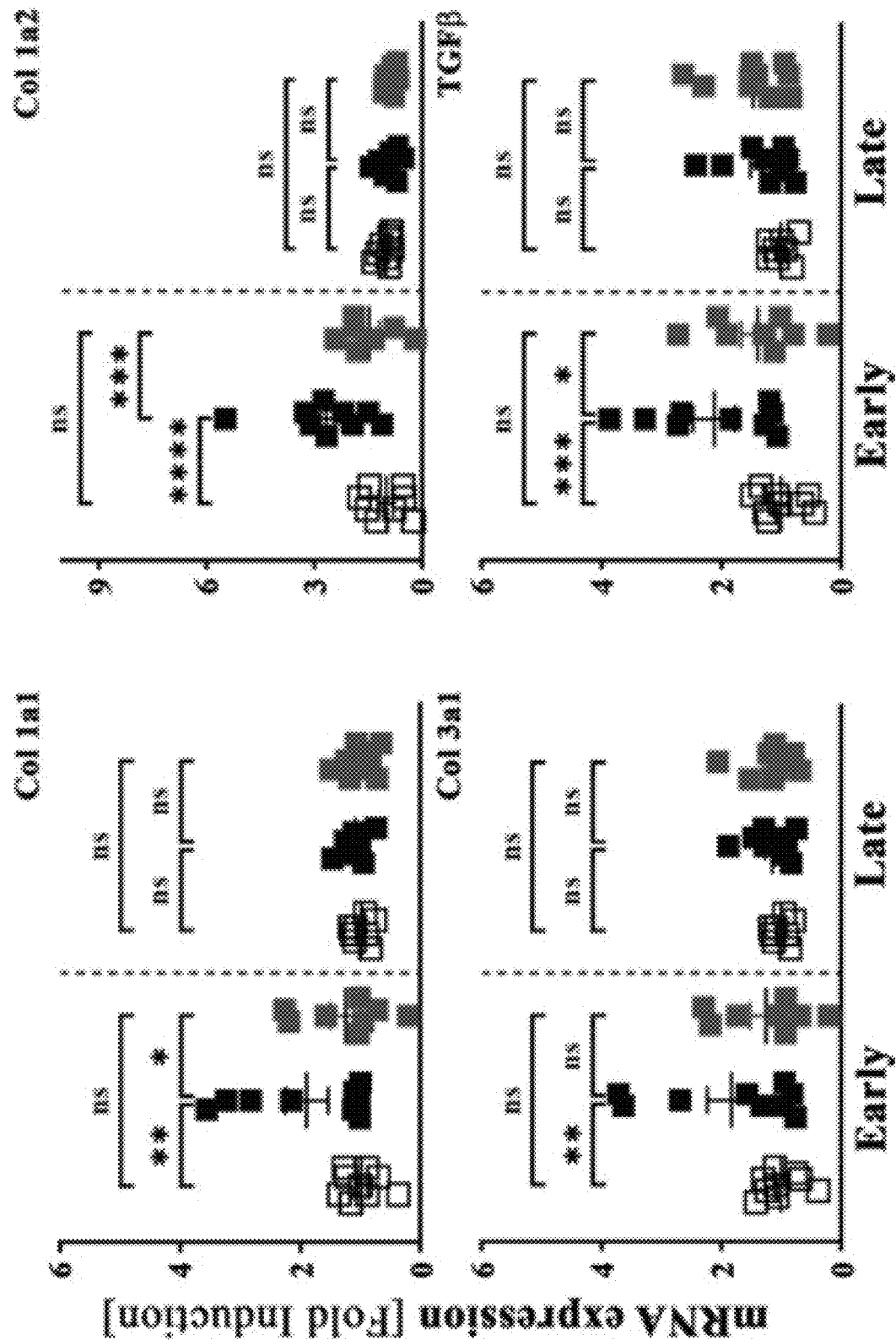

Additionally, qPCR was performed for fibrosis-associated genes and pro-fibrotic markers on RNA extracted from the mouse prostate tissues. Expression levels of collagen-1a1, -1a2, and -3a1, which are extracellular markers of fibrosis as well as TGFβ, a well-known pro-fibrotic signaling molecule (44), were evaluated. Upon CP1 instillation, a significant upregulation of mRNA expression for all four markers in the prostates of CP1-infected mice compared to control mice at day 14 post-infection was seen (FIG. 6E). Interestingly, when CP1-infected mice were treated with CrS+CeHCl, RNA extracted from the prostates of these mice show significantly decreased levels of expression of Collagen-1a1, -1a2 as well as TGFβ in the "early treatment" group (FIG. 6E), but not for Collagen-3a1. While some mild upregulation in the mRNA of these four pro-fibrotic markers in the prostates of the CP1 infected mice at day 35 post-infection was observed, this is not significant; and neither are there any significant changes upon treatment with CrS+CeHCl.

Figure 7B:
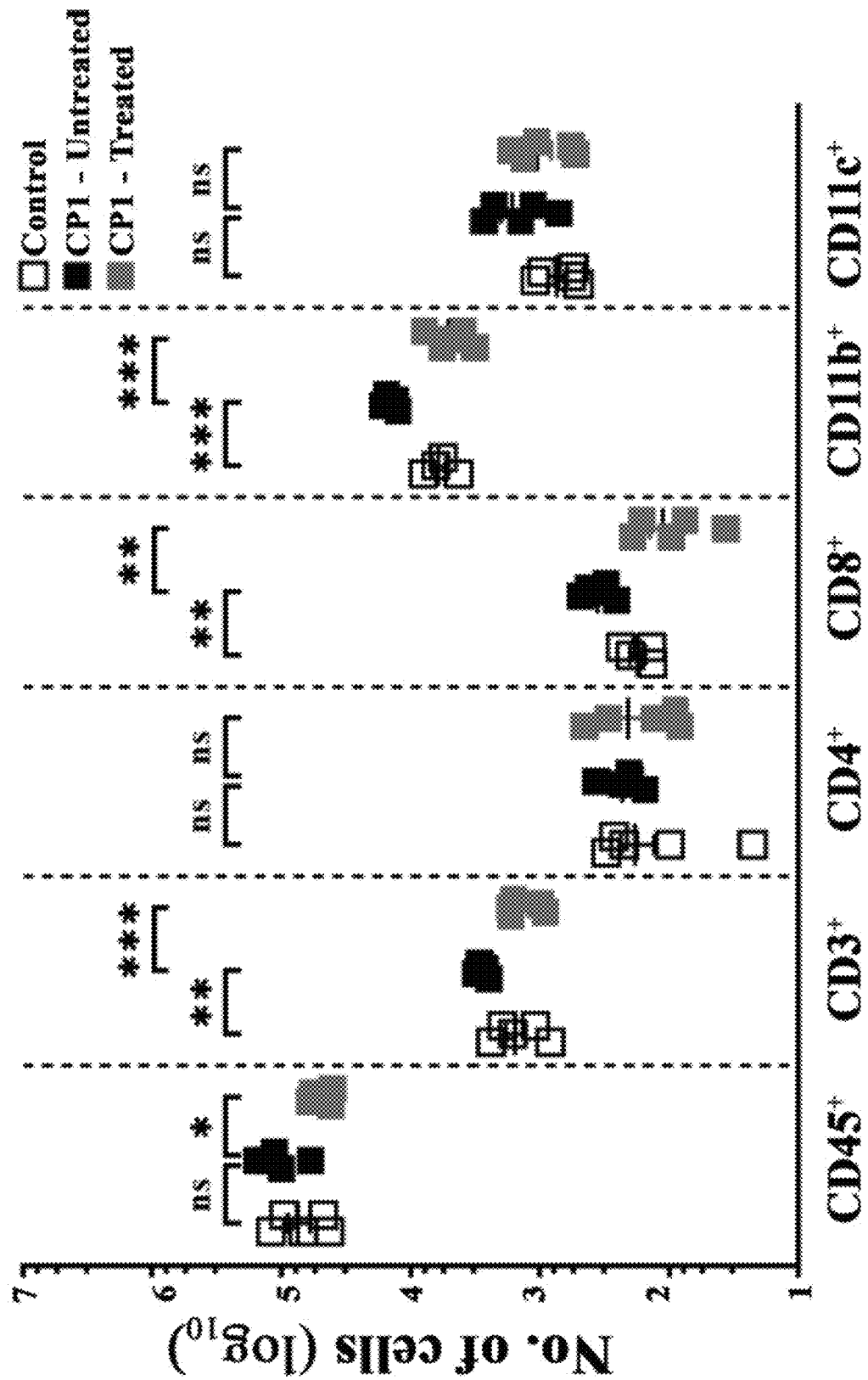

Mast Cell Inhibition Alters the Immune Cell Skewing and Inhibits Type-2 Cytokine Expression in the Prostates of CP1 Infected Mice Activation of mast cells releases a plethora of mediators that are important in triggering the infiltration of immune cells as well as inducing tissue repair after injury (14, 15, 18, 20). Chemokines secreted from the mast cells acting within the prostatic epithelium and stroma provide signals that contribute to increased numbers of B and T lymphocytes and macrophages in the prostates of patients with BPH (45). To assess the effect of the mast cell combination therapy on immune cell infiltrates, flow cytometry was performed on prostates of CP1-infected mice, and immune cell populations were identified and gated as shown in FIG. 7A. As seen in FIG. 7B, at day 35 post CP1 instillation, an increase in the numbers of immune cell infiltrates in the prostates of CP1-infected mice (as seen by the total numbers of $CD45^+$ cells) was observed, which is significantly decreased to levels comparable to that of control mice upon treatment with CrS+CeHCl. CP1-infection significantly increased the numbers of total $CD3^+$ T cells, as well as $CD8^+$ T cells in the prostates of mice. Mast cell inhibition (treatment with CrS+CeHCl) significantly decreased the numbers of total $CD3^+$ T cells as well as $CD8^+$ T cells to numbers similar to those in control mice. Furthermore, upon CP1 instillation, there is a significant increase in numbers of $CD11b^+$ macrophages and a modest increase in $CD11c^+$ dendritic cells in prostates compared to control mice, and upon treatment with CrS+CeHCl the numbers of $CD11b^+$ macrophages significantly decreased to numbers similar to those of control mice (FIG. 7B). These observations were observed in the "early treatment" group as well, albeit to a lesser extent considering that CP1 instillation does not trigger immune cell infiltration early during infection of C57BL/6 mice (Table 2). As seen in Table 2, in the "early treatment" group upon CrS+CeHCl treatment of CP1-infected mice, we observe a significant decrease in the numbers of CD11b+ macrophages, as well as CD4+ and CD8+ T cells compared to CP1-infected mice.

TABLE 2

Immune cell infiltrates in the prostate of CP1 infected mice with and without CrS + CeHCl combination treatment.

| | Treatments | | |
| --- | --- | --- | --- |
| | CP1- Untreated | CP1 + Treatment | |
| | (no. of cells) | | unpaired |
| Cell types | Mean | SD | T-Test |
| CD45+ Lymphocytes | 23024 ± 10122 | 20780 ± 11296 | 0.6223 n.s. |
| CD3+ T cells | 3197 ± 3201 | 1666 ± 466.8 | 0.3805 n.s. |
| CD4+ T cells | 505 ± 45.26 | 343.8 ± 82.27 | 0.0139 * |
| CD8+ T cells | 1122 ± 235.2 | 655.5 ± 169.7 | 0.0182 * |
| B220+ B cells | 329 ± 351.3 | 181 ± 87.64 | 0.4449 n.s. |
| CD11b+ monocytes/macrophages | 2800 ± 1138 | 1315 ± 300.6 | 0.0451 * |
| CD11c+ dendritic cells | 3171 ± 1808 | 1218 ± 148 | 0.0747 # |

Number of infiltrating cells in the prostate of CP1 infected C57BL/6 mice with or without CrS+CeHCl treatment at "early treatment" [day 14 post-infection]. Data shows mean numbers and standard deviations with N=4 mice per group. Unpaired T-Test values are also indicated.

Figure 8:
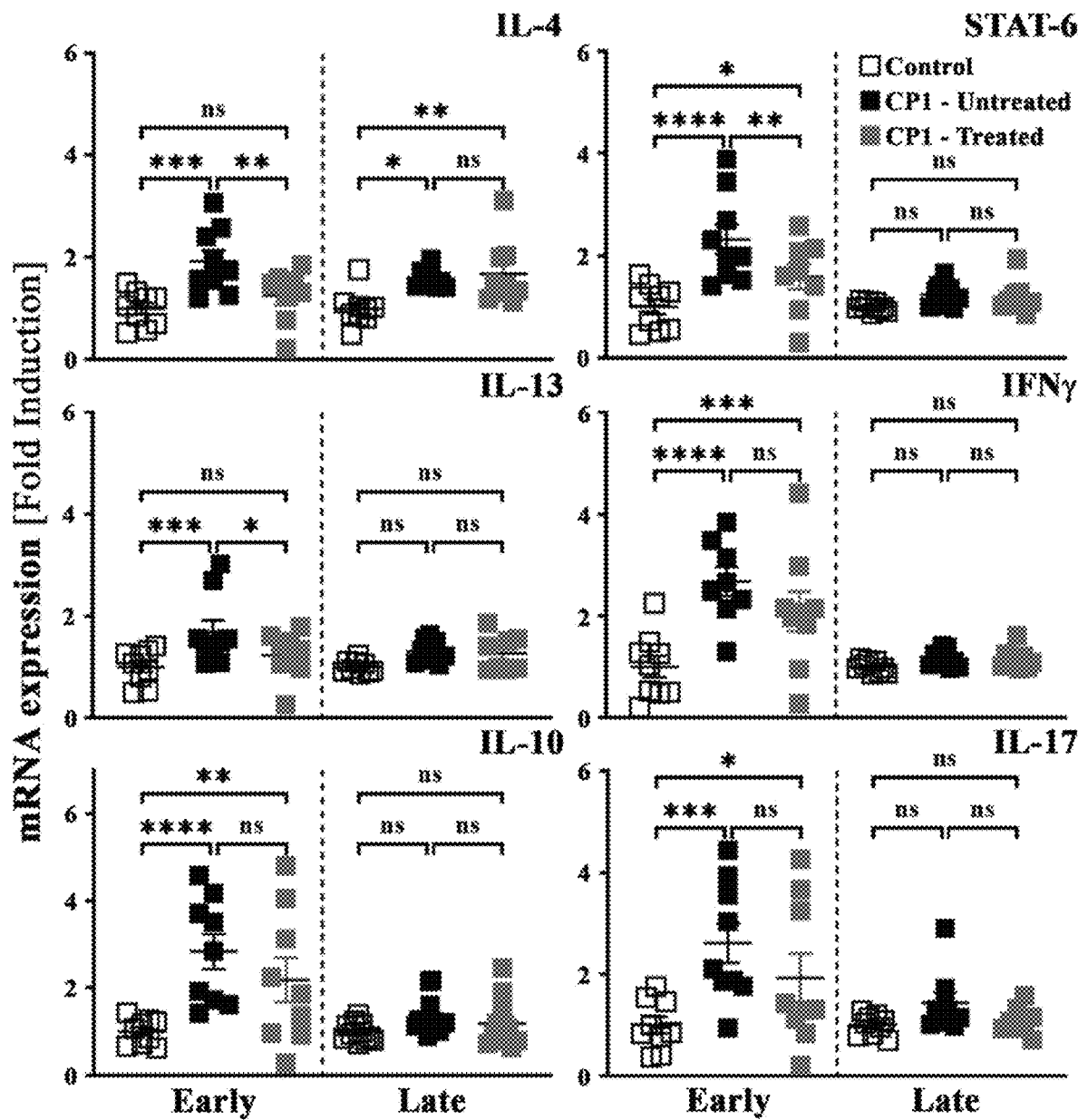
FIG. 8. Prostates of CP1 infected mice treated with CrS+CeHCl show attenuated expression of type-2 cytokine gene expression. Whole prostates from control, CP1 infected mice, and CrS+CeHCl treated CP1 infected mice at 14 ("early") and 35 ("late") days' post CP1 infection were lysed in TRIzol™. RNA was isolated, converted to cDNA, and subjected to real-time PCR analysis with the respective gene primers. The mRNA expression levels are normalized to GAPDH mRNA levels for each sample and the data are represented as fold change over control (Mean±SEM; each dot represents an individual mouse; *$p<0.05$, $p<0.01$, *$p<0.001$, ****$p<0.0001$; one-way ANOVA Fisher's LSD test).
Figure 12:
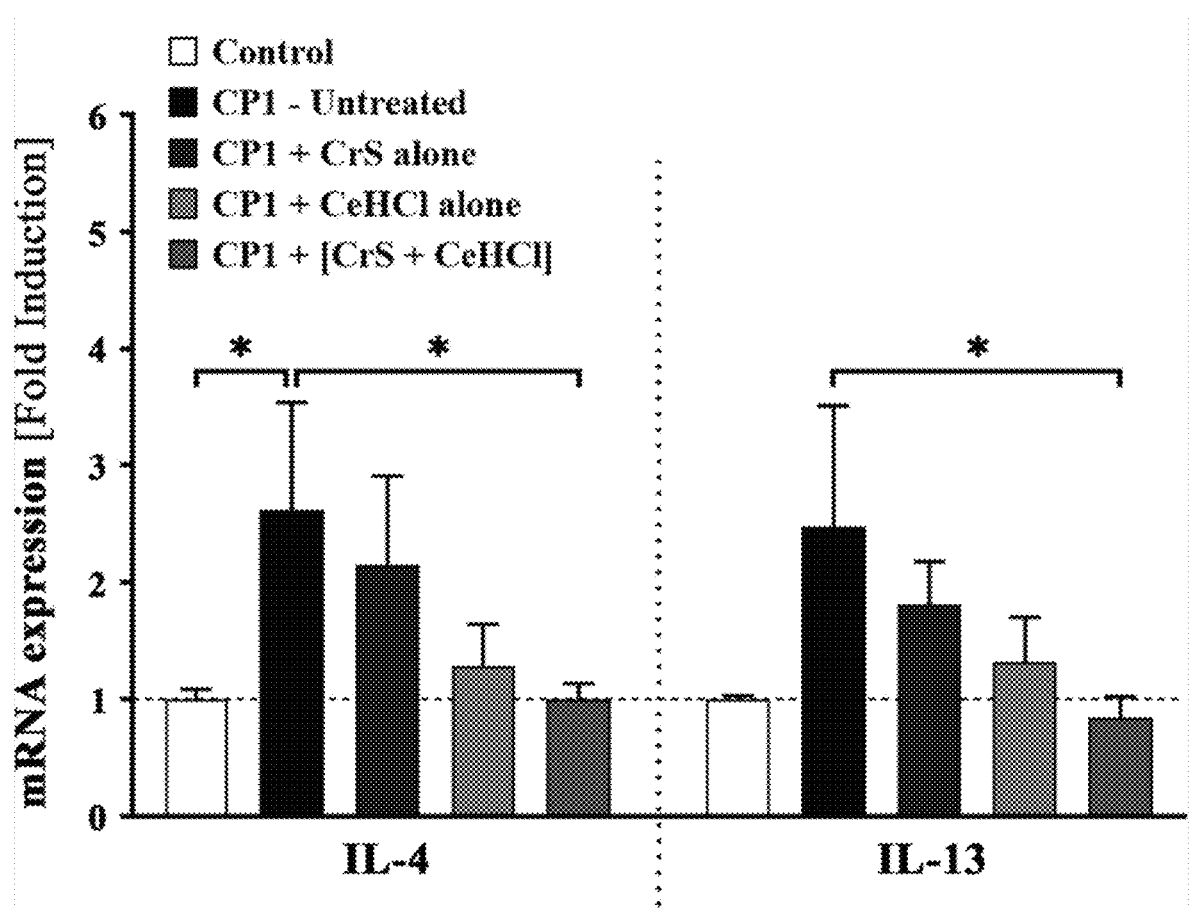
FIG. 12. Histamine 1 receptor antagonist and cromolyn sodium administration shows synergistic attenuation of type 2 cytokine gene expression in prostates of CP1-infected mice. Whole prostates from control, CP1 infected mice, CP1 infected mice with CrS treatment alone, CP1 infected mice with CeHCl treatment alone and CrS+CeHCl treated CP1 infected mice at 35 ("late") days' post CP1 infection were lysed in TRIzol™. RNA was isolated, converted to cDNA, and subjected to real-time PCR analysis with the respective gene primers. The mRNA expression levels are normalized to GAPDH mRNA levels for each sample and the data are represented as fold change over control (Mean±SEM; *$p<0.05$; two-way ANOVA Fisher's LSD test).

To assess the impact of mast cell inhibition therapy on type-2 associated cytokines, qPCR was performed for cytokine transcripts from prostates obtained from control, CP1-infected untreated and CrS+CeHCl treated mice (48). As seen in FIG. 8, in the "early" treatment; and to a lesser extent in the "late" treatment groups; a significant increase in the transcript levels of IL-4 and IL-13 (type-2 associated cytokines) as well as an upregulation of STAT6 (a key signal transduction molecule associated with Th2 polarization (49, 50)) was observed in prostates of CP1-infected mice compared to controls. Upon treatment with CrS+CeHCl, the three markers show significantly reduced transcript levels compared to CP1-infected mice alone in the "early" treatment group. Moreover, when mice were administered single drug treatment of CrS alone or CeHCl alone, treatment with CrS alone reduced the gene expression levels of IL-4 and IL-13 to negligible levels. Treatment with H1 receptor antagonist, CeHCl alone reduced the gene expression levels of IL-4 and IL-13 to a modest but non-significant levels in the prostates of CP1-infected mice. The combination treatment showed synergism and significantly reduced the gene expression of both IL-4 and IL-13 in the prostates of CP1-infected mice (FIG. 12). While the gene expression of other cytokines like IFNγ and IL-17 (associated with type-1 and type-3 immune responses, respectively), and IL-10, a negative regulator of T-cell activation, are significantly upregulated in the prostates upon CP1 instillation in the "early" treatment group. The combination treatment with CrS+CeHCl does not cause any significant changes to their transcript levels in comparison with CP1-infected mice (FIG. 8). These data show that the mast cell combination therapy inhibits type-2 cytokine skewing of the immune response in the prostates of mice induced by CP1 instillation.

Figure 9B:
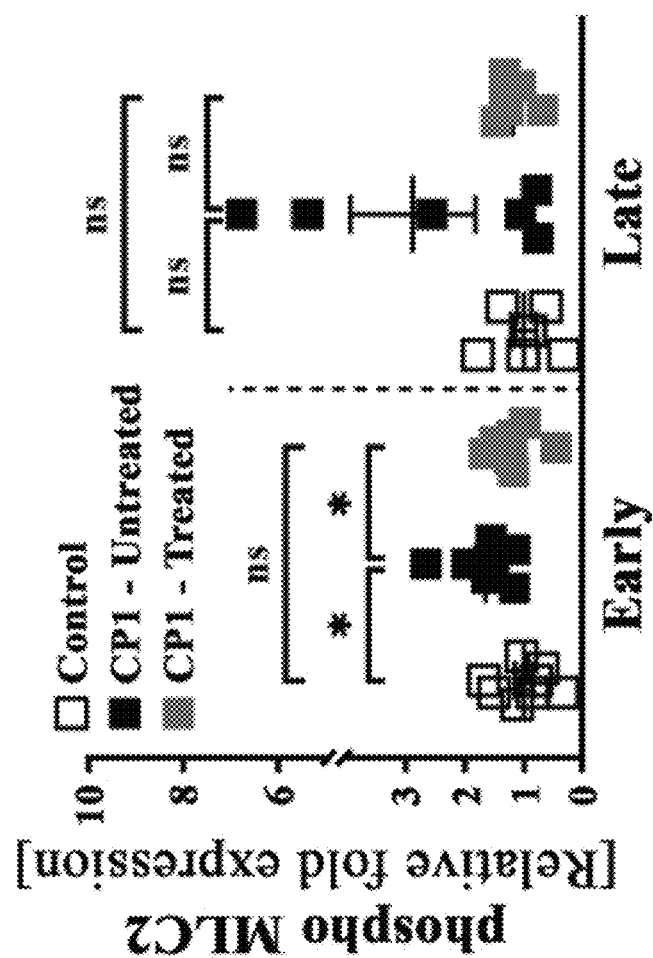
FIG. 9A-B. Mast cell inhibition during CP1-induced LUTS attenuates MLC2 phosphorylation in the prostates of mice. Whole prostates from control, CP1 infected mice, and CrS+CeHCl treated CP1 infected mice at 14 ("early") and 35 ("late") days' post CP1 infection were lysed in 1×RIPA lysis buffer.
Figure 9A:
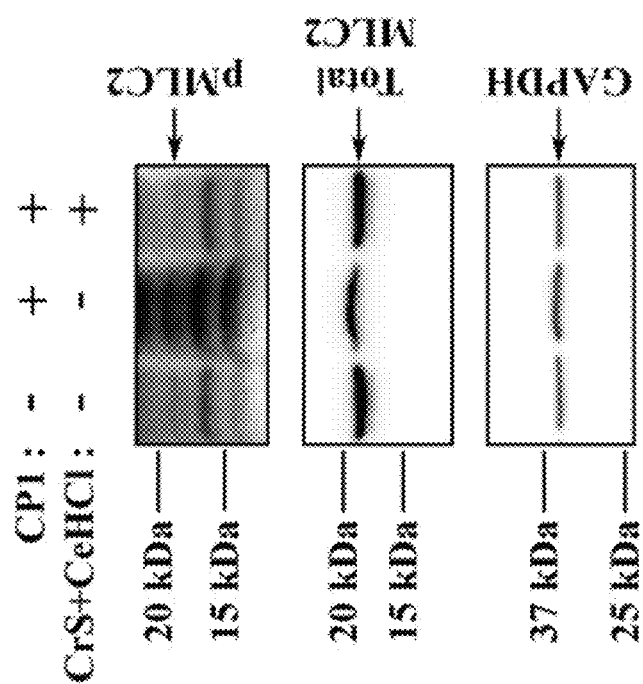

Mast Cell Inhibition Attenuates Phosphorylation of MLC2 in the Prostates, a Marker for Smooth Muscle Cell Contraction, in CP1-Infected Mice As combination treatment is shown herein to interfere with the release of mast cell proteases and tryptases, the consequences of the combination treatment on smooth muscle cell contraction were next evaluated. Smooth muscle cell contraction was evaluated by assessing the phosphorylation status of myosin light chain (MLC)-2, phosphorylation and de-phosphorylation of which regulates muscle contraction and relaxation respectively (52-54), in the prostates from control, CP1-infected untreated and CrS+CeHCl treated mice. As seen in FIG. 9A, upon CP1 instillation in mice, prostate lysates show an elevated level of MLC2 phosphorylation as compared to control mice in the "early treatment" group. Interestingly, in the "early treatment" group, mast cell inhibition causes a significant decrease in the levels of phosphorylated MLC2 in prostate lysates (FIG. 9A). FIG. 9B shows the quantitation by densitometry analysis of the western blot photomicrographs from multiple mice from both "early" and "late" treatment groups. In contrast to what was observed in the "early" treatment group, at later points post CP1 instillation, no significant increase in the levels of phosphorylated MLC2 compared to control mice was observed in prostate lysates. There are no significant differences in phosphorylated MLC2 levels in CP1 infected mice upon mast cell inhibition (FIG. 9B). The data suggest that the mast cell inhibition is effective in reducing smooth muscle cell contraction in the prostates of CP1 infected mice.

Discussion

The pathogenesis of LUTS associated with BPH can be broken down into three facets: the epithelial compartment where hyperplasia of the epithelial cells occurs, the stromal compartment where immune cell infiltration and inflammation cause potential fibrosis, and lastly the smooth muscle compartment where smooth muscle cell contraction occurs (13, 39). An inflammatory insult, sterile inflammation, aging-related factors, or stress-induced hormonal changes, may trigger a dysregulation in any or all these compartments leading to the development and progression of LUTS associated with BPH (4, 5, 7-10). Herein, using an E. coli (CP1) infection induced model of LUTS, the importance of mast cells in the development and progression of urinary dysfunctions was assessed.

CP1 infection in C57BL/6 mice model triggers prostate inflammation, increased immune cell infiltration, urinary dysfunction, and fibrosis. The CP1 infection in C57BL/6 mice does not induce pain (28, 29). The similarities between the urinary dysfunction associated with CP1 infection induced mouse model and LUTS in human BPH extends to increased presence of mast cells in the prostates (especially the dorso-lateral lobe) of the mice as well.

Here, the data demonstrates that CP1 infection triggers type-1, type-2, and type-3 cytokine gene expression. Moreover, combination treatment was specifically able to attenuate type-2 (IL-4, IL-13) cytokines as well as STAT-6 gene expression. Without wishing to be bound by theory, these findings can be explained by two different possible mechanisms. The combination treatment may directly affect the ability of the mast cells to produce and release type-2 cytokines upon activation and degranulation. Secondarily, in synergy with the first proposed mechanism, the administration of H1RA acts as an immunomodulator in the Th1/Th2 imbalance in the diseased prostate and in this model dampens the production of type-2 cytokines by Th2 CD4+ T cells as well as prevents Th2 differentiation and infiltration. The ability of the combination treatment to attenuate STAT-6 alongside IL-4 and IL-13 cytokine gene expression, suggests suppressing the downstream signaling of mast cell mediators through the administration of H1RA directly or indirectly skews the CD4$^{+ve}$ T lymphocytes away from a Th2 cell type. It is likely that the effect of administration of H1RA is due to a combination of at least these two possible mechanisms. This immunomodulatory effect can be seen in the dampening of fibrosis development in prostate tissue. Interestingly, administration of H1RA alone does have a modest effect on IL-4 and IL-13 cytokine gene expression suggesting that administration of individual drug alone might have a profound effect in the prevention of the progression of LUTS.

An unexpected and very surprising observation from mast cell inhibition in the CP1-induced mouse model of LUTS is the ability of the combination treatment to inhibit increased presence of immune cells in the prostates of mice. A plethora chemokines and mitogens are released from mast cells in the context of inflammation, allergy, and infection (14, 18) and in some cases, chemokine release occurs independent of mast cell degranulation (60). The absence of increased immune cells in the prostates of CP1 infected mice upon mast cell inhibition could suggest that they either inhibit infiltration of immune cells in the prostates of these mice, or that they do not provide growth factors, cytokines, and mitogens necessary for the proliferation of the immune infiltrates. In either scenario, these finding are evidence that mast cells might be playing an upstream role in this CP1 infection model of LUTS in mice which precedes immune cell skewing and fibrosis in the prostates of mice. H1RA acts on multiple cell types other than mast cells such as T cells, B cells, endothelial cells, neutrophils, dendritic cells and mast cells (61). The activation of H1 receptors in these multiple cell types leads to different aspects of immune activation such as Th1/Th2 skewing, enhanced B cell proliferation and macrophage polarization. The observations herein in regards to decreased fibrosis and skewing of the immune response in the prostate could be a combination of the drugs acting on these various different cell types.

Mast cell released mediators including histamine, proteases, tryptases, chymases, and leukotrienes have been implicated to play a critical role in smooth muscle cell function, apoptosis, and contraction (15). These mast cell mediators act on PAR2 as well as histamine 1 receptors and play a role in triggering smooth muscle cell contraction (59, 61). Little is understood about the role of mast cell released factors in prostates of patients with BPH and its effects on smooth muscle cell contraction. PAR2 is a gene that is ubiquitously expressed in most tissues in the human body, and PAR2 is expressed at high levels in the smooth muscle cells of both murine and human prostates. PAR2 activation by these mast cell proteases, triggers downstream $Ca^{2+}$ dependent prostate smooth muscle cell contraction (27, 66). It is possible that PAR2 inhibitors along with α-blockers (drugs that inhibit α-adrenergic receptor signaling) could be used in conjunction to treat urinary symptoms in patients with chronic prostatitis/chronic pelvic pain syndrome (CP/CPPS) and BPH (27). However, the observations herein provide a potentially more favorable therapeutic target upstream of PAR2 blockade, along with alleviating fibrosis and inflammation.

Figure 10:
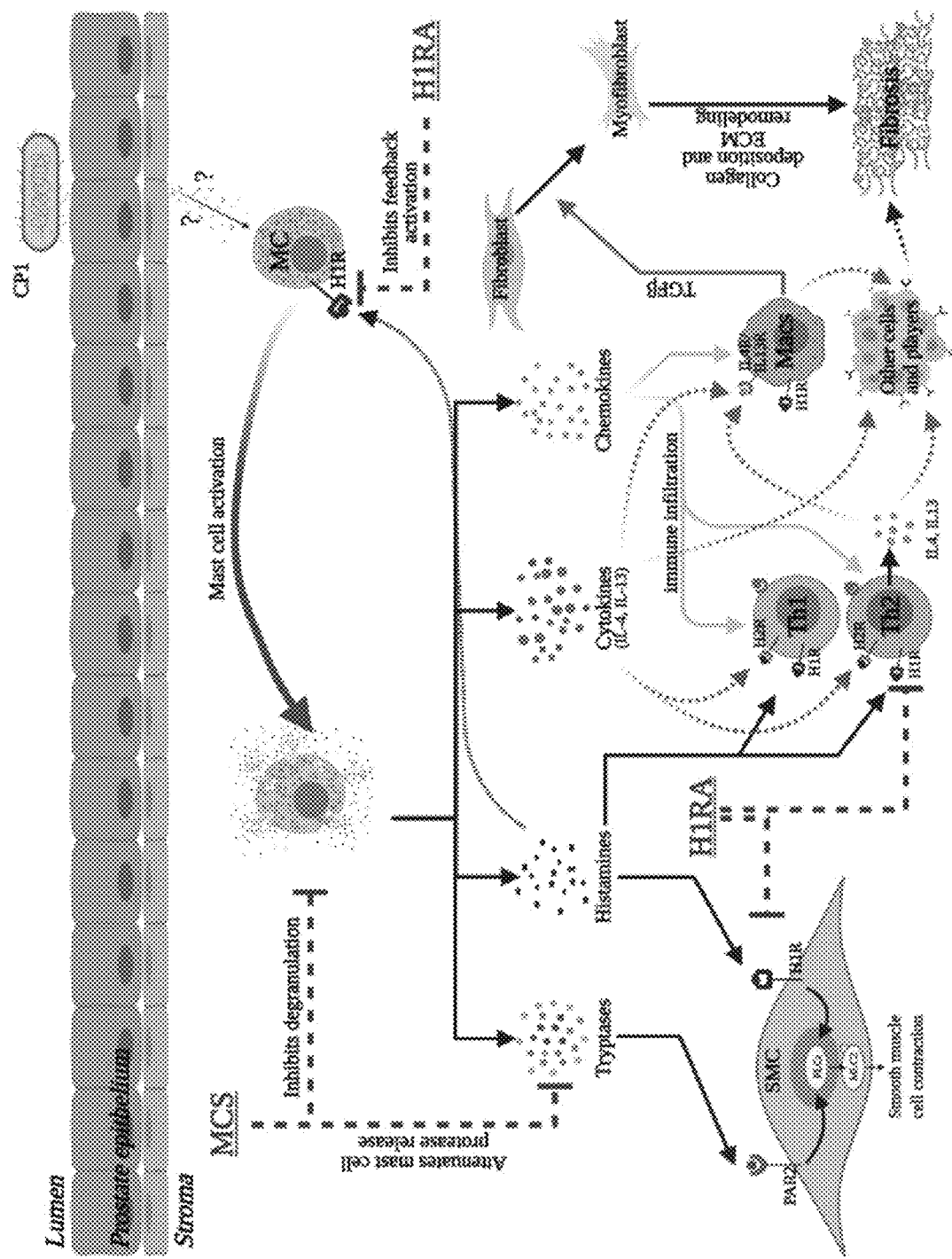
FIG. 10. Schematic illustration of the crucial multifaceted role played by prostate mast cells in facilitating prostatic inflammation, fibrosis, and smooth muscle contraction in the development of lower urinary tract symptoms. Intraurethral instillation of CP1 in mice triggers epithelial tissue damage that induces the release of as yet unknown factors that lead to an increase in mast cell (MC) numbers and its activation in the mouse prostate stroma. The activated mast cells in turn release a plethora of factors which include tryptases (and other proteases), histamines, cytokines (including IL-4, IL-13), and chemokines. The tryptases and histamine released from mast cells act on smooth muscle cells (SMC), via protease-activated receptor 2 (PAR2) and histamine 1 receptors (H1R) respectively, leading to a PLC mediated regulation of smooth muscle cell contraction. Histamine released from activated mast cells also trigger a feedback loop to further activate mast cells through histamine receptors on mast cells. The chemokines released trigger increased immune cell infiltration and proliferation. The cytokines released from mast cells lead to activation of T helper type 1 (Th1), Th2, Th17 cells, dendritic cells and macrophages (Macs). The histamines released from mast cells in turn act on H1R and H2R on Th1 and Th2 cells modulating type-1/type-2 cytokine production leading to a hyper-inflammatory environment. IL-4 and IL-13 released from mast cells and Th2 cells act on macrophages (Macs) and cause macrophage polarization leading to release of TGFβ which causes primed resident fibroblasts to differentiate into myofibroblasts that release collagen and other matric proteins leading to extracellular matrix (ECM) remodeling and fibrosis. Also, the cytokines released from mast cells, T cells, macrophages and other cells might interact with immune and non-immune cells to promote fibrosis independent of myofibroblasts transition. The combination treatment for mast cell inhibition which include mast cell stabilizer (MCS) and histamine 1 receptor antagonist (H1RA) act on multiple different cell types at multiple levels of these crucial aspects and regulate the tissue environment in a CP1-infected mouse prostate.
Figure 11A:
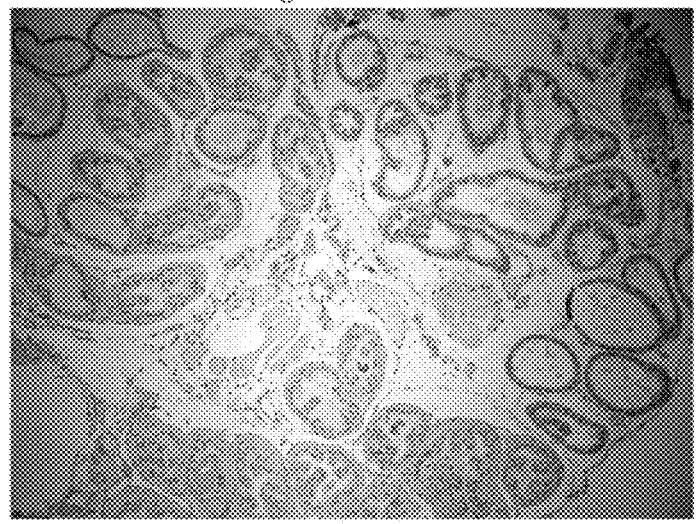
FIG. 11A-D. CP1 instillation does not trigger an increase in basophil numbers in the 869 prostate of mice. Dorsolateral prostate tissue sections were stained with mMCP8 at 35-days post CP1 infection for assessing the presence of basophils. Representative IHC images of mMCP8 stained dorsolateral prostate sections from (FIG. 11A) negative control (FIG. 11B) positive control using prostate tissue from a prostate cancer model, (FIG. 11C) control PBS instilled, and (FIG. 11D) CP1 infected mice at 35-day post instillation imaged at 10× magnification. A 40× magnification of position control (FIG. 11B) is also inset in the image showing presence of basophils. Arrow heads mark the areas of infiltrating basophils.
Figure 11B:
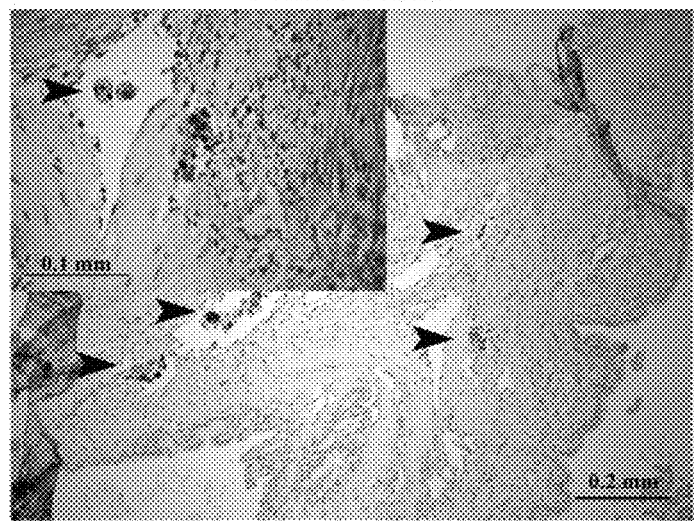
Figure 11C:
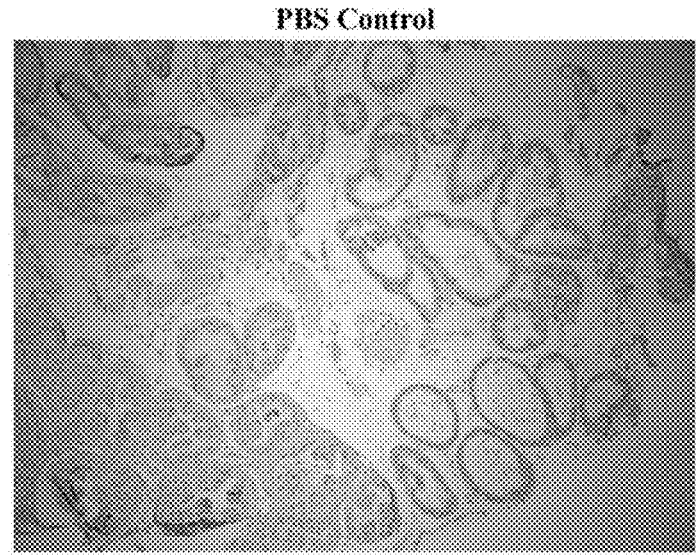
Figure 11D:
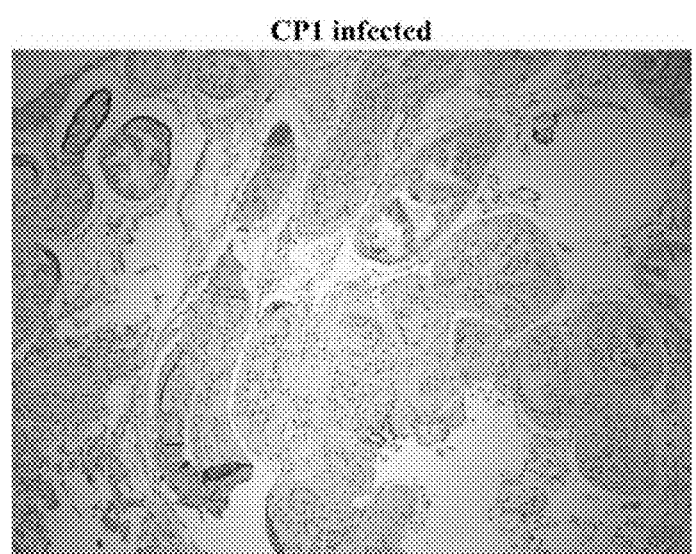

The key findings of this study show that mast cell numbers and its activity are increased in prostates of patients with BPH/LUTS and in CP1-infected mice showing symptoms of LUTS. Mast cell inhibition, through a combination of MCS and H1RA, alleviates the urinary dysfunction in CP1-infected mice. Mast cell inhibition triggers decreased inflammation and fibrosis, attenuation in smooth muscle cell contraction, and a decrease in immune infiltrates in the prostates of CP1-infected mice (FIG. 10). An in-depth assessment of the importance of mast cells in the development and progression of urinary dysfunction can be addressed using genetic knockout (mast cell-deficient W-sash c-kit mutant Kit$^{W-sh/W-sh}$ mice) approaches (67-69). These approaches, however, could be confounded by the impact of mast cells on innate immune homeostasis. The combination therapy approach of administration of a MCS along with H1RA provides a model wherein overactive mast cells are dampened in the prostate to alleviate both the histopathological changes and the physiological effects of urinary dysfunction.

Taken together, the data presented herein demonstrates that mast cells play a role in the pathogenesis of voiding dysfunction in an uropathogenic *E. coli* induced mouse model of LUTS. Mast cells have been shown to be present in increased numbers in the prostates of patients with BPH/LUTS. Whether these mast cells are functionally active remains to be determined. Herein it is demonstrated that mast cell inhibition, through a combination of MCS and H1RA, alleviates the urinary dysfunction in CP1-infected mice. Mice treated with this combination also show reduced prostatic fibrosis, less infiltration of immune cells, decreased inflammation, along with potentially easing smooth muscle contraction in the prostates. The observations from this study show that blockade of mast cell function is therapeutically effective for ameliorating voiding dysfunction. These studies have important translational implications for men diagnosed with BPH associated LUTS.

Example 2

Experiments were conducted during development of embodiments herein to evaluate the effect of inhibition of mast cells and H1R on conditions, such as, chronic prostatitis (CP) and chronic pelvic pain syndrome (CPPS). A clinical study was performed in CP/CPPS patients to evaluate the use of a mast cell stabilizer and a selective H1 receptor antagonist to reduce the levels of prostate mast cell tryptase and affect symptoms in patients.

Experiments were conducted during development of embodiments herein to demonstrate that treatment of CP/CPPS patients having elevated mast cell tryptase in their expressed prostatic secretions with mast cell stabilizer cromolyn sodium and histamine 1 receptor antagnosit cetirizine hydrochloride reduces mast tryptase to control levels observed in healthy humans. Studies were conducted under an FDA-approved physician-initiated IND exemption.

Potential participants were identified during urology visits on the basis of accepted definitions for CPPS. Subjects were patients using the following exclusion and inclusion criteria:
Inclusion Criteria
Male ages 21-80 years old
Diagnosed with Category III Chronic Pelvic Pain Syndrome
Patients reporting pain or discomfort in any of the 8 domains of the NIH Chronic Prostatitis Symptom Index (NIH-CPSI).
CP/CPPS symptoms must have been present for the majority of the time during any 3 months in the previous 6 months.
Mast cell tryptase levels in EPS above a control threshold based on healthy men.

Exclusion Criteria

Females

Males <21 and >80 years old

Patients with a known hypersensitivity to cromolyn sodium or cetirizine hydrochloride Patients with impaired renal or hepatic function.

Mast cell tryptase levels in EPS equal to or below a control threshold based on healthy men The primary endpoint for the study was a reduction in mast cell tryptase at the end of treatment compared to levels observed before administration of the study drug. Secondary endpoints were significant reductions in the NIH-CPSI scores.

Figure 13:
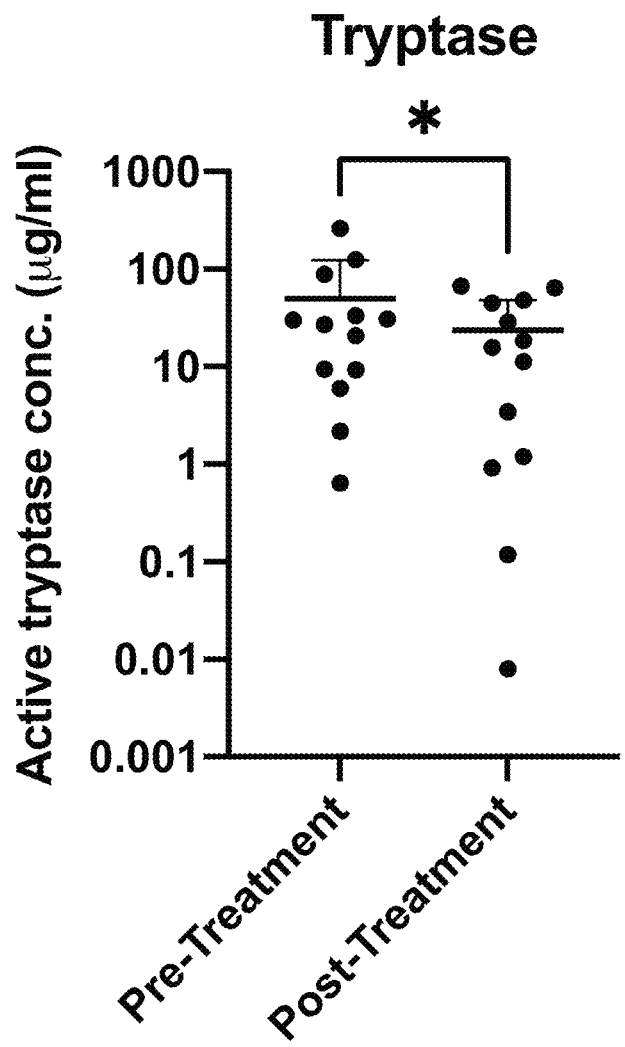
FIG. 13. A significant reduction in tryptase levels was observed in patients treated with combination therapy.

The study demonstrated that combination inhibition of mast cells and H1R activity reduces mast cell tryptase levels in CP/CPPS patients. A three-week period of inhibition of mast cell degranulation as well as histamine 1 receptor activity resulted in a significant inhibition of mast cell tryptase levels in CP/CPPS patients. All patients were enrolled in the study using elevated mast cell tryptase in expressed prostatic fluid/voided bladder urine 3 as an entry criteria. At three weeks after initiation of treatment, a significant reduction in tryptase levels was observed in treated patients (FIG. 13; p=0.0317, Ratio paired t test, two tailed).

Figure 14:
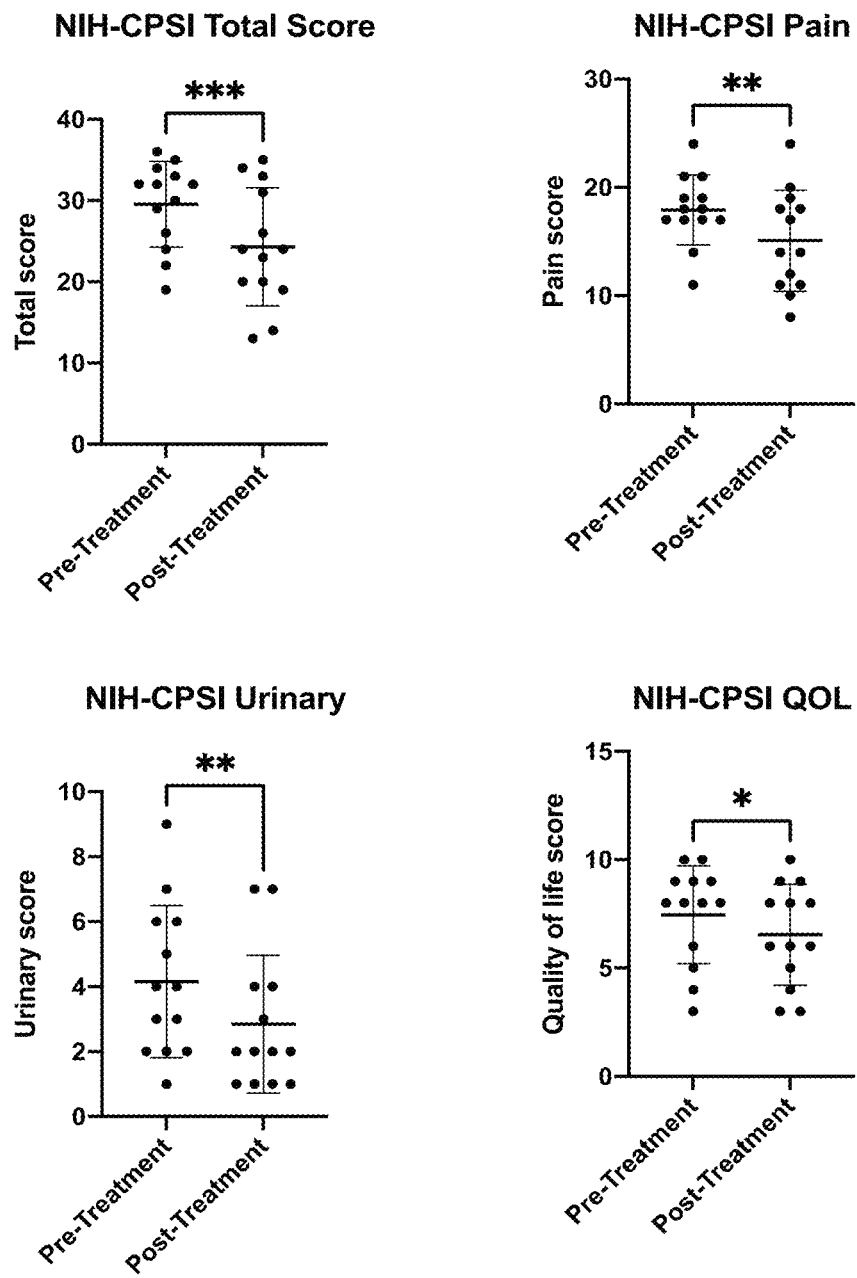
FIG. 14. Significant reductions in the total NIH-CPSI score and in pain, urinary and QOL domains, were observed in patients treated with combination therapy.

The study demonstrated that reduction in mast cell tryptase levels is associated with improvement in CP/CPPS patient symptoms. CP/CPPS patients at entry into the trial completed a validated symptom questionnaire—the National Institutes of Health Chronic Prostatitis Symptom Index (NIH-CPSI). Patients then self-administered the treatment regime and completed the questionnaire weekly till the final administration at week three. The change in total score (8-49) was monitored, as well as the change in individual domains of the NIH-CPSI, namely, Pain (8-28), Urinary (0-10) and Quality of Life (QOL) (0-11) from pre-treatment to post-treatment at end of week three. A highly significant reduction in the total NIH-CPSI score (p=0.0009, two tailed paired t test), and significant reduction in the pain (p=0.0047), urinary (0.0038) and QOL (p=0.0160) domains, were observed (FIG. 14).

The results from the clinical study in CP/CPPS patients indicates that mast cell tryptase can be utilized to identify patients with a diagnosis of CP/CPPS who have an underlying disease pathogenesis involving aberrant activation of mast cells. Furthermore, results from the therapeutic inhibition of degranulation and mast cell function in patients indicates that reduction of mast cell tryptase via therapeutic treatment is associated with a concurrent reduction in the critical symptoms of CP/CPPS.

The invention claimed is:

1. A method of treating benign prostatic hyperplasia (BPH) in a subject, comprising providing to the subject one or more inhibitors of mast cell function, wherein the one or more inhibitors of mast cell function comprise cromolyn sodium cetirizine.

2. The method of claim 1, wherein the condition is benign prostatic hyperplasia associated with lower urinary tract symptoms.

3. The method of claim 1, wherein the subject is a human.

* * * * *

SEQUENCE LISTING

```
<160> NUMBER OF SEQ ID NOS: 22

<210> SEQ ID NO 1
<211> LENGTH: 21
<212> TYPE: DNA
<213> ORGANISM: Artificial sequence
<220> FEATURE:
<223> OTHER INFORMATION: synthetic

<400> SEQUENCE: 1
gctgacctgc tggattacat t                                             21

<210> SEQ ID NO 2
<211> LENGTH: 21
<212> TYPE: DNA
<213> ORGANISM: Artificial sequence
<220> FEATURE:
<223> OTHER INFORMATION: synthetic

<400> SEQUENCE: 2
gttgagagat catctccacc a                                             21

<210> SEQ ID NO 3
<211> LENGTH: 20
<212> TYPE: DNA
<213> ORGANISM: Artificial sequence
<220> FEATURE:
<223> OTHER INFORMATION: synthetic

<400> SEQUENCE: 3
ccatatccac ggatgcgaca                                               20

<210> SEQ ID NO 4
<211> LENGTH: 20
<212> TYPE: DNA
<213> ORGANISM: Artificial sequence
<220> FEATURE:
<223> OTHER INFORMATION: synthetic

<400> SEQUENCE: 4
```

-continued cgttgctgtg aggacgtttg                                                   20

<210> SEQ ID NO 5
<211> LENGTH: 20
<212> TYPE: DNA
<213> ORGANISM: Artificial sequence
<220> FEATURE:
<223> OTHER INFORMATION: synthetic

<400> SEQUENCE: 5
gtatggagtg tggacctggc                                                   20

<210> SEQ ID NO 6
<211> LENGTH: 20
<212> TYPE: DNA
<213> ORGANISM: Artificial sequence
<220> FEATURE:
<223> OTHER INFORMATION: synthetic

<400> SEQUENCE: 6
tctgggtcct gtagatggca                                                   20

<210> SEQ ID NO 7
<211> LENGTH: 22
<212> TYPE: DNA
<213> ORGANISM: Artificial sequence
<220> FEATURE:
<223> OTHER INFORMATION: synthetic

<400> SEQUENCE: 7
acgacaacag cctcagtgtg ga                                                22

<210> SEQ ID NO 8
<211> LENGTH: 22
<212> TYPE: DNA
<213> ORGANISM: Artificial sequence
<220> FEATURE:
<223> OTHER INFORMATION: synthetic

<400> SEQUENCE: 8
caggacacca tcaaaccact gc                                                22

<210> SEQ ID NO 9
<211> LENGTH: 20
<212> TYPE: DNA
<213> ORGANISM: Artificial sequence
<220> FEATURE:
<223> OTHER INFORMATION: synthetic

<400> SEQUENCE: 9
acggcacagt cattgaaagc                                                   20

<210> SEQ ID NO 10
<211> LENGTH: 20
<212> TYPE: DNA
<213> ORGANISM: Artificial sequence
<220> FEATURE:
<223> OTHER INFORMATION: synthetic

<400> SEQUENCE: 10
accatccttt tgccagttcc                                                   20

<210> SEQ ID NO 11
<211> LENGTH: 22
<212> TYPE: DNA

```
<213> ORGANISM: Artificial sequence
<220> FEATURE:
<223> OTHER INFORMATION: synthetic

<400> SEQUENCE: 11
cagactacct caaccgttcc ac                                          22

<210> SEQ ID NO 12
<211> LENGTH: 22
<212> TYPE: DNA
<213> ORGANISM: Artificial sequence
<220> FEATURE:
<223> OTHER INFORMATION: synthetic

<400> SEQUENCE: 12
tccagctttc cctccgcatt ga                                          22

<210> SEQ ID NO 13
<211> LENGTH: 23
<212> TYPE: DNA
<213> ORGANISM: Artificial sequence
<220> FEATURE:
<223> OTHER INFORMATION: synthetic

<400> SEQUENCE: 13
atttgaattc cctgggtgag aag                                         23

<210> SEQ ID NO 14
<211> LENGTH: 22
<212> TYPE: DNA
<213> ORGANISM: Artificial sequence
<220> FEATURE:
<223> OTHER INFORMATION: synthetic

<400> SEQUENCE: 14
cacaggggag aaatcgatga ca                                          22

<210> SEQ ID NO 15
<211> LENGTH: 20
<212> TYPE: DNA
<213> ORGANISM: Artificial sequence
<220> FEATURE:
<223> OTHER INFORMATION: synthetic

<400> SEQUENCE: 15
cgatggattc ccgttcgagt                                             20

<210> SEQ ID NO 16
<211> LENGTH: 20
<212> TYPE: DNA
<213> ORGANISM: Artificial sequence
<220> FEATURE:
<223> OTHER INFORMATION: synthetic

<400> SEQUENCE: 16
gaggcctcgg tggacattag                                             20

<210> SEQ ID NO 17
<211> LENGTH: 20
<212> TYPE: DNA
<213> ORGANISM: Artificial sequence
<220> FEATURE:
<223> OTHER INFORMATION: synthetic

<400> SEQUENCE: 17
agtcgatggc tgctccaaaa                                             20
```

```
<210> SEQ ID NO 18
<211> LENGTH: 20
<212> TYPE: DNA
<213> ORGANISM: Artificial sequence
<220> FEATURE:
<223> OTHER INFORMATION: synthetic

<400> SEQUENCE: 18
gcaatgtcaa ggaacggcag                                                 20

<210> SEQ ID NO 19
<211> LENGTH: 20
<212> TYPE: DNA
<213> ORGANISM: Artificial sequence
<220> FEATURE:
<223> OTHER INFORMATION: synthetic

<400> SEQUENCE: 19
aagggcgaag atggcaaaga                                                 20

<210> SEQ ID NO 20
<211> LENGTH: 20
<212> TYPE: DNA
<213> ORGANISM: Artificial sequence
<220> FEATURE:
<223> OTHER INFORMATION: synthetic

<400> SEQUENCE: 20
agccactagg acccctttct                                                 20

<210> SEQ ID NO 21
<211> LENGTH: 20
<212> TYPE: DNA
<213> ORGANISM: Artificial sequence
<220> FEATURE:
<223> OTHER INFORMATION: synthetic

<400> SEQUENCE: 21
ggactctcca cctgcaagac                                                 20

<210> SEQ ID NO 22
<211> LENGTH: 20
<212> TYPE: DNA
<213> ORGANISM: Artificial sequence
<220> FEATURE:
<223> OTHER INFORMATION: synthetic

<400> SEQUENCE: 22
ctggcgagcc ttagtttgga                                                 20
```